(12) United States Patent
Sato et al.

(10) Patent No.: US 7,378,480 B2
(45) Date of Patent: May 27, 2008

(54) POLYMERIZABLE COMPOUND, POLYMER COMPOUND, COMPOSITION USING SUCH COMPOUND, AND IMAGE FORMING METHOD AND APPARATUS

(75) Inventors: Koichi Sato, Kanagawa (JP); Ikuo Nakazawa, Kanagawa (JP); Sakae Suda, Kanagawa (JP); Masayuki Ikegami, Kanagawa (JP); Keiichiro Tsubaki, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 641 days.

(21) Appl. No.: 10/927,347

(22) Filed: Aug. 25, 2004

(65) Prior Publication Data
US 2005/0027037 A1 Feb. 3, 2005

Related U.S. Application Data

(63) Continuation of application No. PCT/JP03/02476, filed on Mar. 4, 2003.

(30) Foreign Application Priority Data

Mar. 6, 2002 (JP) .............................. 2002-061067
Sep. 27, 2002 (JP) .............................. 2002-283448

(51) Int. Cl.
C08F 16/16 (2006.01)
C08L 53/00 (2006.01)
C09D 11/02 (2006.01)
C09D 11/10 (2006.01)

(52) U.S. Cl. ...................... 526/334; 526/320; 526/326; 526/332; 526/333; 524/505; 524/612; 106/31.13; 106/31.27; 106/31.28; 106/31.6; 106/31.85; 106/31.86

(58) Field of Classification Search ................ 523/160, 523/161; 106/31.13, 31.27, 31.28, 31.6, 106/31.85, 31.86; 526/334, 333, 332, 326, 526/320; 524/505, 612
See application file for complete search history.

(56) References Cited

U.S. PATENT DOCUMENTS 5,198,319 A * 3/1993 Kato ........................... 430/96
5,399,631 A * 3/1995 Egawa et al. ............. 525/328.9
5,883,157 A * 3/1999 Yamashita et al. .......... 523/161
6,391,923 B1 * 5/2002 Pollmann et al. ........... 514/714
7,067,590 B2 * 6/2006 Sato et al. ................... 525/299

FOREIGN PATENT DOCUMENTS

| DE | 2263963 | 12/1974 |
|---|---|---|
| EP | 0 761 782 | 3/1997 |
| EP | 1243624 A1 * | 8/2002 |
| JP | 11080221 | 3/1999 |
| JP | 11322866 | 11/1999 |
| JP | 11322942 | 11/1999 |
| JP | 2001-072895 | 3/2001 |
| WO | WO 2004058903 A1 * | 7/2004 |

OTHER PUBLICATIONS

International Search Reporet dated May 13, 2003.
Takeuchi et al.; "Living Cationic Polymerization of Ethyl 2-(Vinyloxy) ethoxyacetate: A vinyl Ether with an Ether and an Ester Function in the Pendant"; *Journal of Polymer Science: Part A: Polymer Chemistry*; vol. 27; pp. 3303-3314; (1989).

* cited by examiner

*Primary Examiner*—Sanza L. McClendon
(74) *Attorney, Agent, or Firm*—Morgan & Finnegan, LLP

(57) ABSTRACT

Polymeric compounds suitable for ink and toner compositions, and image forming methods and apparatus using an ink or toner composition containing such a polymer compound, and particularly to a polymer compound having a repeating unit structure represented by the general formula

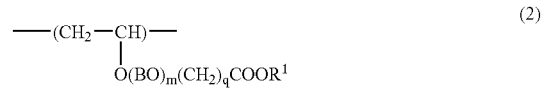

wherein B is a linear or branched alkylene group having 1 to 15 carbon atoms and may be substituted, m is an integer of 1 to 30, q is an integer of 2 to 30, and $R^1$ is hydrogen, an alkyl group which may be substituted, or an aromatic ring structure which may be substituted, with the proviso that when m is a plural number, the B groups may be different from each other, ink and toner compositions containing the polymer compound, a solvent or dispersion medium and a coloring material, and image forming methods and image forming apparatus using such a composition.

6 Claims, 1 Drawing Sheet

POLYMERIZABLE COMPOUND, POLYMER COMPOUND, COMPOSITION USING SUCH COMPOUND, AND IMAGE FORMING METHOD AND APPARATUS

This application is a continuation of International Application No. PCT/JP03/02476, filed on Mar. 4, 2003, which claims the benefit of Japanese Patent Application Nos. as follows:
1) 2002-061067 filed on Mar. 6, 2002
2) 2002-283448 filed on Sep. 27, 2002

BACKGROUND OF THE INVENTION

1. Field of the Invention

The present invention relates to novel polymerizable compounds and polymer compounds that are useful as various kinds of functional materials, compositions using such a polymer compound, and image forming methods and image forming apparatus, and particularly to ink compositions and toner compositions using such a polymer compound together with a solvent or dispersion medium and a coloring material, and various image forming methods and image forming apparatus using such a composition.

2. Related Background Art

An ink composition or toner composition has heretofore been prepared by dissolving or dispersing a coloring material in a solvent. In these compositions, various kinds of polymer materials are preferably used. For example, styrylic, acrylic and methacrylic polymer compounds are used. In a color material composition using a solvent and/or water as a base material, it is generally attempted to preferably utilize a polymer material having an ionic functional group to improve the dispersibility of a coloring material such as a pigment.

On the other hand, polymer compounds having a main poly(vinyl ether) chain have also been known as polymer materials having a flexible polymer chain. However, it is scarcely conducted to introduce an ionic functional group into a repeating unit of such a polymer compound. "Journal of Polymer Science: Part A, Polymer Chemistry", Vol. 27, (1989) slightly describes that carboxylic acids and esters thereof described on pages 3303 to 3314 in the Journal have such a possibility. As the stability of such compounds, higher stability is required under the circumstances.

SUMMARY OF THE INVENTION

The present invention has been made in view of the foregoing circumstances and has as its object the provision of a polymer compound suitable for improving the dispersibility of a coloring material and solid matter in an ink composition or toner composition.

Another object of the present invention is to provide an image forming method and image forming apparatus using a recording material such as an ink composition or toner composition using the above polymer compound.

The present inventors have carried out an extensive investigation as to the above-described prior art and problems, thus leading to completion of the present invention.

The above objects can be achieved by the present invention described below.

In a first aspect of the present invention, there is provided a polymerizable compound represented by the general formula

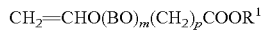  (1)

wherein B is a linear or branched alkylene group which has 1 to 15 carbon atoms and may be substituted, m is an integer of from 1 to 30, p is an integer of from 2 to 30, and $R^1$ is hydrogen, an alkyl group which may be substituted, or an aromatic ring structure which may be substituted, with the proviso that when m is a plural number, the B groups may be different from each other.

In a second aspect of the present invention, there is provided a polymer compound having a repeating unit structure represented by the general formula

  (2)

wherein B is a linear or branched alkylene group which has 1 to 15 carbon atoms and may be substituted, m is an integer of from 1 to 30, q is an integer of from 2 to 30, and $R^1$ is hydrogen, an alkyl group which may be substituted, or an aromatic ring structure which may be substituted, with the proviso that when m is a plural number, the B groups may be different from each other.

In a third aspect of the present invention, there is provided a polymer compound having a repeating unit structure represented by the general formula

  (3)

wherein B is a linear or branched alkylene group which has 1 to 15 carbon atoms and may be substituted, m is an integer of from 1 to 30, q is an integer of from 2 to 30, and M is a monovalent or polyvalent metal cation, with the proviso that when m is a plural number, the B groups may be different from each other.

In a fourth aspect of the present invention, there is provided a composition comprising a polymer compound having at least one selected from repeating unit structures represented by general formulae

  (12)

wherein B is a linear or branched alkylene group which has 1 to 15 carbon atoms and may be substituted, m is an integer of from 1 to 30, t is an integer of from 1 to 30, and $R^1$ is hydrogen, an alkyl group which may be substituted, or an aromatic ring structure which may be substituted, with the proviso that when m is a plural number, the B groups may be different from each other, and

  (13)

wherein B is a linear or branched alkylene group which has 1 to 15 carbon atoms and may be substituted, m is an integer of from 1 to 30, t is an integer of from 1 to 30, and M is a monovalent or polyvalent metal cation, with the proviso that when m is a plural number, the B groups may be different from each other.

In a fifth aspect of the present invention, there is provided a recording material comprising a solvent or dispersion medium, a coloring material and the polymer compound having at least one selected from the repeating unit structures represented by the general formulae (12) and (13).

In a sixth aspect of the present invention, there is provided a toner composition comprising a dispersion medium, a coloring material and the polymer compound having at least one selected from the repeating unit structures represented by the general formulae (12) and (13).

In a seventh aspect of the present invention, there is provided an ink composition comprising a solvent, a coloring material and the polymer compound having at least one selected from the repeating unit structures represented by the general formulae (12) and (13).

In an eighth aspect of the present invention, there is provided an image forming method comprising applying the ink composition according to the seventh aspect to a medium to form an image on the medium.

In the image forming method, the ink composition may preferably be applied by an ink-jet recording system.

In a ninth aspect of the present invention, there is provided an image forming apparatus used in the image forming method described above.

In a tenth aspect of present invention, there is provided a block polymer compound having a repeating unit structure represented by the general formula

(14)

wherein B is a linear or branched alkylene group which has 1 to 15 carbon atoms and may be substituted, m is an integer of from 1 to 30, q is an integer of from 2 to 30, and $R^1$ is hydrogen, an alkyl group which may be substituted, or an aromatic ring structure which may be substituted, with the proviso that when m is a plural number, the B groups may be different from each other.

In an eleventh aspect of the present invention, there is provided a block polymer compound having a repeating unit structure represented by the general formula

(15)

wherein B is a linear or branched alkylene group which has 1 to 15 carbon atoms and may be substituted, m is an integer of from 1 to 30, q is an integer of from 2 to 30, and M is a monovalent or polyvalent metal cation, with the proviso that when m is a plural number, the B groups may be different from each other.

In a twelfth aspect of the present invention, there is provided a composition comprising the block polymer compound according to the tenth or eleventh aspect.

In a thirteenth aspect of the present invention, there is provided a composition comprising a solvent or dispersion medium, a functional material and the block polymer compound according to the tenth or eleventh aspect.

In a fourteenth aspect of the present invention, there is provided a composition comprising a block polymer compound of a poly(vinyl ether) repeating unit structure containing at least one selected from an aliphatic carboxylic acid ester, an aliphatic carboxylic acid and an aliphatic carboxylic acid salt therein, a solvent or dispersion medium and a coloring material.

In a fifteenth aspect of the present invention, there is provided a toner composition comprising a dispersion medium, a coloring material and the block polymer compound according to the tenth or eleventh aspect.

In a sixteenth aspect of the present invention, there is provided an ink composition comprising a solvent, a coloring material and the block polymer compound according to the tenth or eleventh aspect.

In a seventeenth aspect of the present invention, there is provided a method of thickening the composition according to any one of the twelfth to sixteenth aspects, which comprises bringing a hydrogen ion or metal cation into contact with such a composition.

In an eighteenth aspect of the present invention, there is provided an image forming method comprising applying the composition according to any one of the twelfth to sixteenth aspects to a recording medium to form an image on the medium.

In a nineteenth aspect of the present invention, there is provided an image forming method comprising ejecting the ink composition according to the sixteenth aspect on a recording medium to form an image on the medium.

In a twentieth aspect of the present invention, there is provided an image forming apparatus used in the image forming method according to the eighteenth or nineteenth aspect to form an image on a recording medium.

DETAILED DESCRIPTION OF THE PREFERRED EMBODIMENTS

Figure 1:
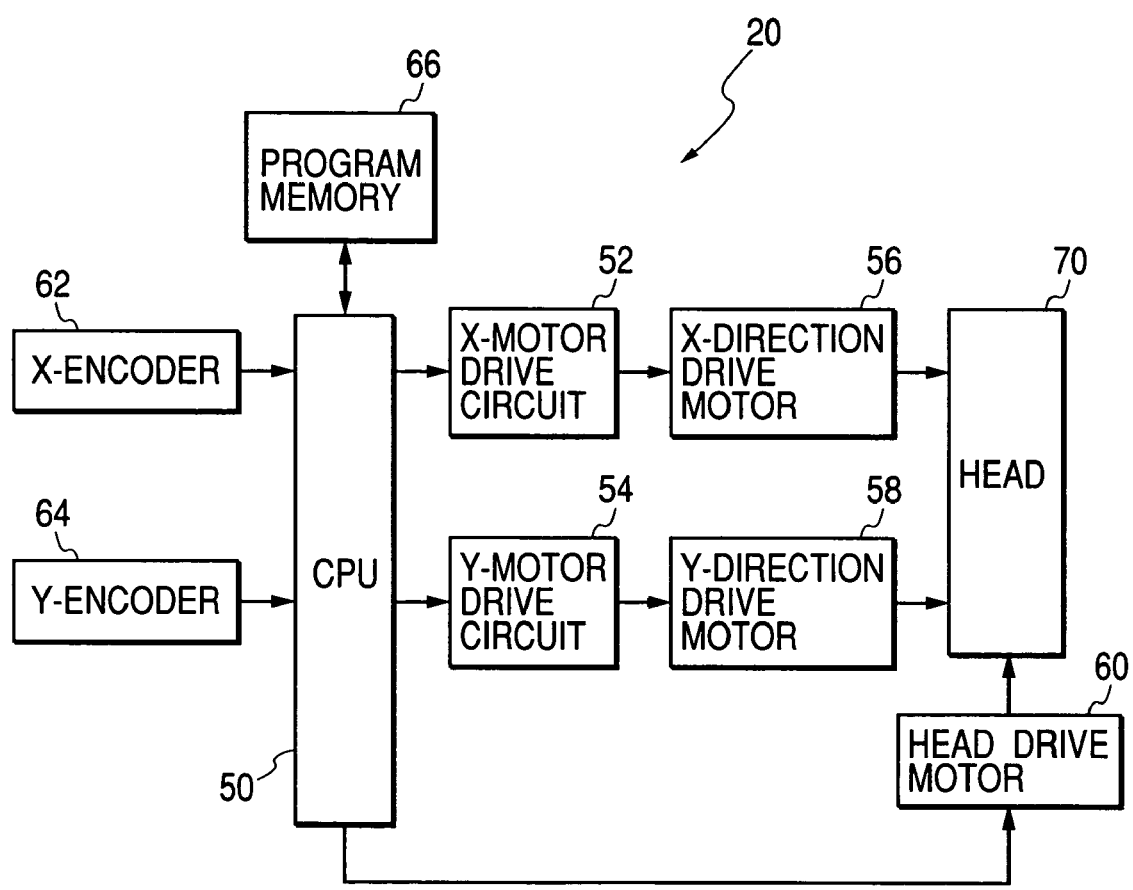
FIG. 1 is a block diagram illustrating the construction of an ink-jet recording apparatus.

The present invention will hereinafter be described in detail.

The polymerizable compound according to an aspect of the present invention is composed of a compound represented by the general formula

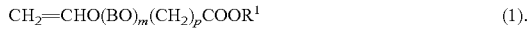

(1).

In the general formula (1), B is a linear or branched alkylene group which has 1 to 15 carbon atoms, preferably 2 to 10 carbon atoms and may be substituted. Examples of the substituent group on the alkylene group include ethylene, propylene and butylene.

m is an integer of from 1 to 30, preferably 1 to 10. When m is a plural number, the respective B groups may be different from each other.

p is an integer of from 2 to 30, preferably 2 to 20.

$R^1$ is hydrogen, an alkyl group which may be substituted, or an aromatic ring structure which may be substituted. The alkyl group is preferably an alkyl group having 1 to 10 carbon atoms. Examples of the aromatic ring structure include phenyl, pyridyl and biphenyl groups. Examples of the substituent group include alkyl and alkoxy groups.

Preferable examples of the polymerizable compound represented by the general formula (1) include compounds represented by the following general formula (4). The compounds represented by the general formula (4) are compounds in which B in the general formula (1) is $(CH_2)_n$.

$$CH_2=CHO[(CH_2)_nO]_m(CH_2)_pCOOR^1 \quad (4)$$

wherein n is an integer of from 1 to 15, and m, p and $R^1$ have the same meanings as described above.

In the polymerizable compound according to the present invention represented by the general formula (1), a feature is that p is 2 or greater. When p is 0 or 1, the stability of such a compound is considerably impaired. On the other hand, the stability when p is 2 or greater becomes considerably preferable. p is preferably 4 or higher, more preferably from 4 to 20.

Specific examples of the polymerizable compound represented by the general formula (1) include compounds described below.

$CH_2=CHOCH_2CH_2O(CH_2)_2COOC_2H_5$ $CH_2=CHOCH_2CH_2O(CH_2)_3COOC_2H_5$ $CH_2=CHOCH_2CH_2O(CH_2)_4COOC_2H_5$ $CH_2=CHOCH_2CH_2O(CH_2)_5COOC_2H_5$ $CH_2=CHOCH_2CH_2O(CH_2)_6COOC_2H_5$ $CH_2=CHOCH_2CH_2O(CH_2)_7COOC_2H_5$ $CH_2=CHOCH_2CH_2O(CH_2)_8COOC_2H_5$ $CH_2=CHOCH_2CH_2O(CH_2)_{10}COOC_2H_5$ $CH_2=CHOCH_2CH_2O(CH_2)_{15}COOC_2H_5$ $CH_2=CHOCH_2CH_2O(CH_2)20COOC_2H_5$ $CH_2=CHOCH_2CH_2O(CH_2)_2COOCH_3$ $CH_2=CHOCH_2CH_2O(CH_2)_3COOCH_3$ $CH_2=CHOCH_2CH_2O(CH_2)_4COOCH_3$ $CH_2=CHOCH_2CH_2O(CH_2)_5COOCH_3$ $CH_2=CHOCH_2CH_2O(CH_2)_6COOCH_3$ $CH_2=CHOCH_2CH_2O(CH_2)_7COOCH_3$ $CH_2=CHOCH_2CH_2O(CH_2)_8COOCH_3$ $CH_2=CHOCH_2CH_2O(CH_2)_{10}COOCH_3$ $CH_2=CHOCH_2CH_2O(CH_2)_{15}COOCH_3$ $CH_2=CHOCH_2CH_2O(CH_2)20COOCH_3$ $CH_2=CHO(CH_2CH_2O)_2(CH_2)_2COOC_2H_5$ $CH_2=CHO(CH_2CH_2O)_3(CH_2)_3COOC_2H_5$ $CH_2=CHO(CH_2CH_2O)_{10}(CH_2)_4COOC_2H_5$ $CH_2=CHO(CH_2CH_2O)_{20}(CH_2)_5COOC_2H_5$ $CH_2=CHO(CH_2CH_2O)_2(CH_2)_6COOC_2H_5$ $CH_2=CHO(CH_2CH_2O)_8(CH_2)_7COOC_2H_5$ $CH_2=CHO(CH_2CH_2O)_5(CH_2)_8COOC_2H_5$ $CH_2=CHO(CH_2CH_2O)_{10}(CH_2)_{10}COOC_2H_5$ $CH_2=CHO(CH_2CH_2O)_{15}(CH_2)_{15}COOC_2H_5$ $CH_2=CHO(CH_2CH_2O)_2(CH_2)20COOC_2H_5$ $CH_2=CHOCH_2CH_2CH_2CH_2CH_2CH_2CH_2O(CH_2)_2COOC_2H_5$ $CH_2=CHOCH_2CH_2CH_2CH_2O(CH_2)_3COOC_2H_5$ $CH_2=CHOCH_2CH_2CH_2CH_2O(CH_2)_4COOC_2H_5$ $CH_2=CHOCH_2CH_2CH_2CH_2CH_2CH_2CH_2O(CH_2)_5COOC_2H_5$ $CH_2=CHOCH_2CH_2CH_2CH_2CH_2CH_2O(CH_2)_6COOC_2H_5$ $CH_2=CHOCH(CH_3)CH_2O(CH_2)_7COOC_2H_5$ $CH_2=CHOCH(CH_3)CH_2O(CH_2)_8COOC_2H_5$ $CH_2=CHOCH_2CH(CH_3)O(CH_2)_{10}COOC_2H_5$ $CH_2=CHOCH(C_2H_5)CH_2O(CH_2)_{15}COOC_2H_5$ $CH_2=CHOCH_2CH(CH_3)O(CH_2)_{20}COOC_2H_5$ $CH_2=CHOCH_2CH_2O(CH_2)_2COOPh$ $CH_2=CHOCH_2CH_2O(CH_2)_3COOPh$ $CH_2=CHOCH_2CH_2O(CH_2)_4COOPyr$ $CH_2=CHOCH_2CH_2CH_2CH_2O(CH_2)_5COOPh$ $CH_2=CHOCH_2CH_2O(CH_2)_6COOPh(OCH_3)$ $CH_2=CHO(CH_2CH_2O)_2(CH_2)_7COOPh(OCH_3)$ $CH_2=CHOCH_2CH_2O(CH_2)_8COOPh(OCH_3)$ $CH_2=CHOCH_2CH_2O(CH_2)_{10}COOPh(OCH_3)$ $CH_2=CHOCH_2CH_2O(CH_2)_{15}COOPh(OCH_3)$ $CH_2=CHOCH_2CH_2O(CH_2)_{20}COOPh(OCH_3)$ wherein Ph is a phenyl group, and Pyr is a pyridyl group.

Typical examples of a synthetic process of the polymerizable compound represented by the general formula (1) include those according to such etherification process as shown by the following reaction scheme.

Reaction Scheme 1:

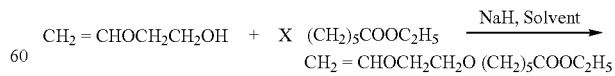

wherein X is a halogen.

In another aspect of the present invention, there is provided a polymer compound having a repeating unit structure represented by the general formula

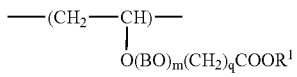
(2)

In the general formula (2), B is a linear or branched alkylene group which has 1 to 15 carbon atoms and may be substituted. m is an integer of from 1 to 30. When m is a plural number, the respective B groups may be different from each other. q is an integer of from 2 to 30. $R^1$ is hydrogen, an alkyl group which may be substituted, or an aromatic ring structure which may be substituted. A preferable range of m and specific examples of B and $R^1$ are the same as in the general formula (1).

Preferable examples of the repeating unit structure represented by the general formula (2) include unit structures represented by the following general formula (5). The unit structures represented by the general formula (5) are unit structures in which B in the general formula (2) is $(CH_2)_n$.

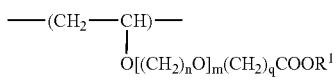
(5)

wherein n is an integer of from 1 to 15, and m, q and $R^1$ have the same meanings as described above.

In the general formula (2) of the present invention represented, a feature is that q is 2 or greater. When q is 0 or 1, the stability of such a polymer compound is considerably impaired. On the other hand, the stability when q is 2 or greater becomes considerably preferable. q is preferably 4 or higher, more preferably from 4 to 20.

Specific examples of the repeating unit structure represented by the general formula (2) include unit structures described below.

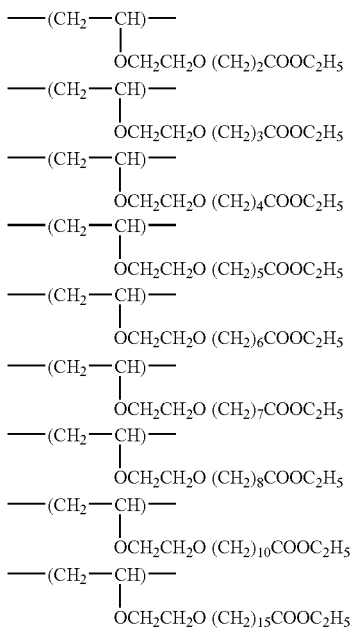

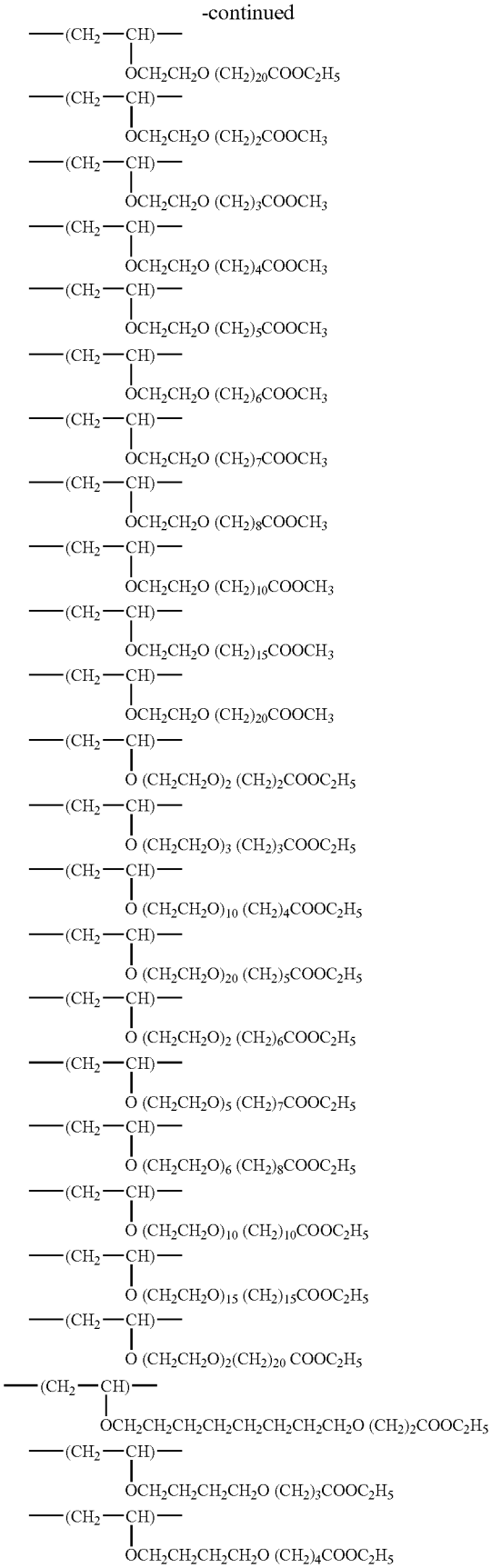

-continued

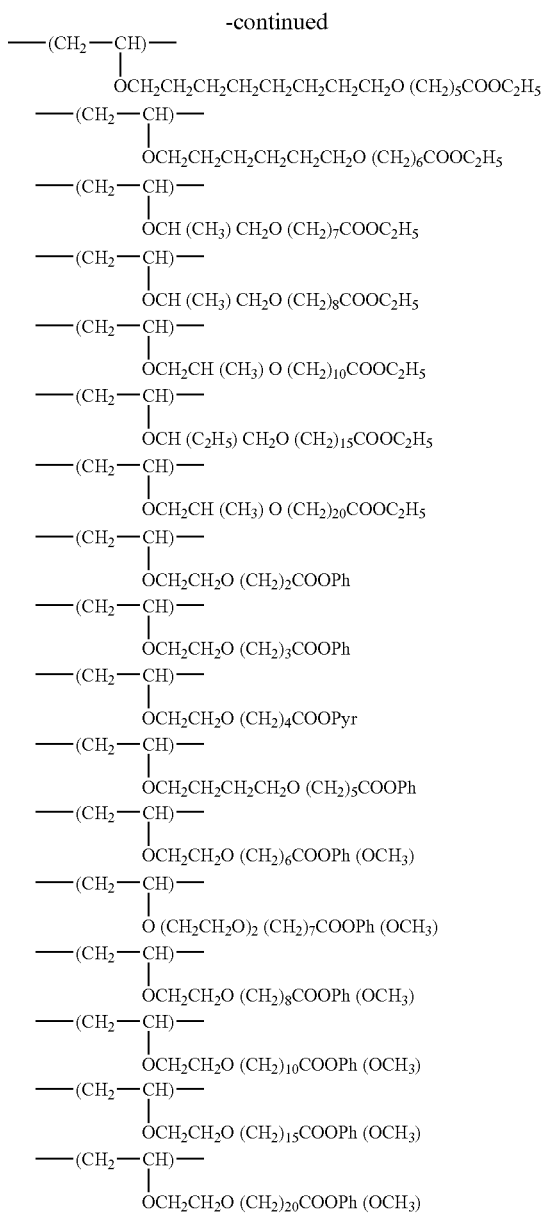

wherein Ph is a phenyl group, and Pyr is a pyridyl group.

The polymer compound having the repeating unit structure represented by the general formula (2) can be obtained by polymerizing, preferably, the polymerizable compound represented by the general formula (1). The polymerization is often mainly performed by cationic polymerization. Examples of an initiator include combinations of a protonic acid such as hydrochloric acid, sulfuric acid, methanesulfonic acid, trifluoroacetic acid, trifluornmethanesulfonic acid or perchloric acid, of a Lewis acid such as $BF_3$, $AlCl_3$, $TiCl_4$, $SnCl_4$, $FeCl_3$, $RAlCl_2$ or $R_{1.5}AlCl_{1.5}$ (R being alkyl) and a cation source (examples of the cation source include adducts of a protonic acid, water, alcohol or vinyl ether and a carboxylic acid). Such an initiator and the polymerizable compound (monomer) represented by the general formula (1) are caused to coexist, whereby the reaction can be allowed to progress to synthesize the polymer compound.

The number average molecular weight of the polymer compound having the repeating unit structure represented by the general formula (2) is from 200 to 10,000,000, preferably from 1,000 to 1,000,000. If the molecular weight exceeds 10,000,000, intrachain and interchain entanglement of such polymer compound becomes too great, and so it is hard to be dispersed in a solvent. If the molecular weight is lower than 200, such a compound may be difficult to exhibit a steric effect as a polymer in some cases because the molecular weight is too low. The polymer compound according to the present invention may be either a homopolymer composed of a sole repeating unit structure or a copolymer composed of a plurality of repeating unit structures.

In a further aspect of the present invention, there is provided a polymer compound having a repeating unit structure represented by the general formula

(3)

In the general formula (3), B is a linear or branched alkylene group which has 1 to 15 carbon atoms and may be substituted. m is an integer of from 1 to 30. When m is a plural number, the respective B groups may be different from each other. q is an integer of from 2 to 30. A preferable range of m and specific examples of B and $R^1$ are the same as in the general formula (1).

M is a monovalent or polyvalent metal cation. Specific examples of M include sodium, potassium and lithium as monovalent cations, and magnesium and calcium as polyvalent cations. When M is a polyvalent cation, M makes a couple with $COO^-$ of the number of its valences.

Preferable examples of the repeating unit structure represented by the general formula (3) include unit structures represented by the following general formula (6). The unit structures represented by the general formula (6) are unit structures in which B in the general formula (3) is $(CH_2)_n$.

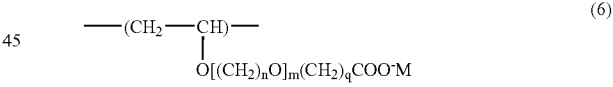

(6)

wherein n an integer of from 1 to 15, and m, q and $R^1$ have the same meanings as described above.

A polymer compound of the present invention having the repeating unit structure of the general formula (3) can be obtained by hydrolyzing terminal ester moieties of a polymer compound having its corresponding repeating unit structure of the general formula (2) with an alkali. The polymer compound can also be obtained by conducting hydrolysis with an acid and treating the hydrolyzed product with an alkali. However, the former process is preferred.

Specific examples of the repeating unit structure represented by the general formula (3) include unit structures described below.

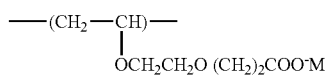

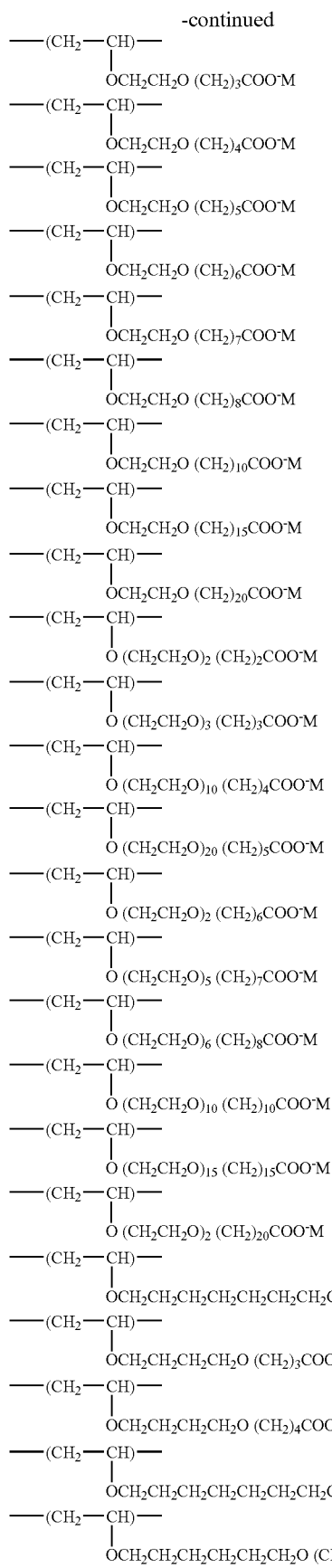

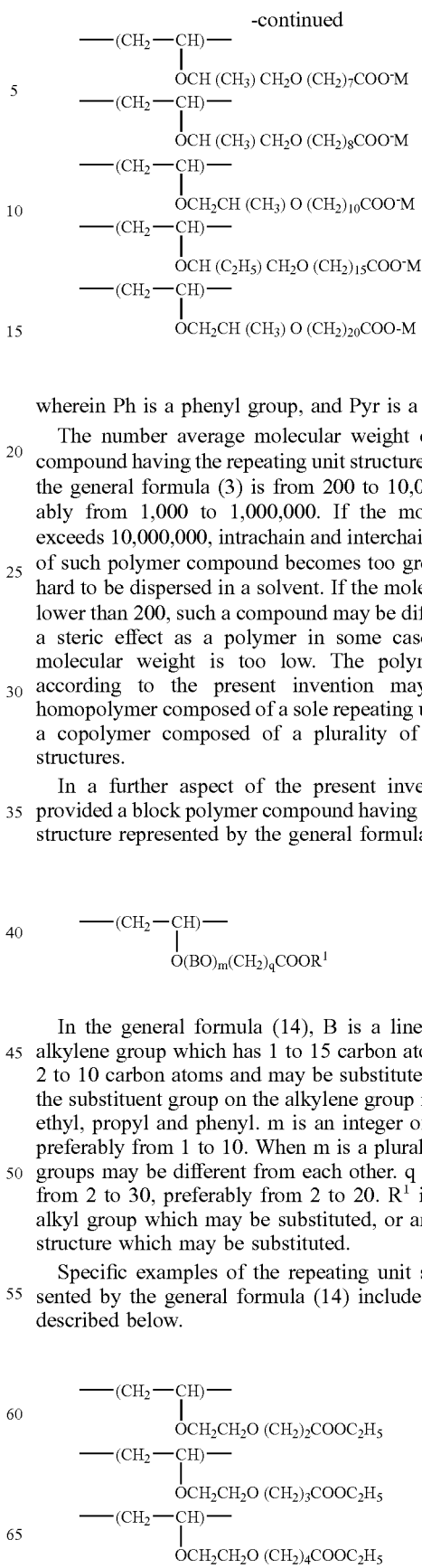

wherein Ph is a phenyl group, and Pyr is a pyridyl group.

The number average molecular weight of the polymer compound having the repeating unit structure represented by the general formula (3) is from 200 to 10,000,000, preferably from 1,000 to 1,000,000. If the molecular weight exceeds 10,000,000, intrachain and interchain entanglement of such polymer compound becomes too great, and so it is hard to be dispersed in a solvent. If the molecular weight is lower than 200, such a compound may be difficult to exhibit a steric effect as a polymer in some cases because the molecular weight is too low. The polymer compound according to the present invention may be either a homopolymer composed of a sole repeating unit structure or a copolymer composed of a plurality of repeating unit structures.

In a further aspect of the present invention, there is provided a block polymer compound having a repeating unit structure represented by the general formula $$—(CH_2—CH)— \atop | \atop O(BO)_m(CH_2)_qCOOR^1 \qquad (14)$$

In the general formula (14), B is a linear or branched alkylene group which has 1 to 15 carbon atoms, preferably 2 to 10 carbon atoms and may be substituted. Examples of the substituent group on the alkylene group include methyl, ethyl, propyl and phenyl. m is an integer of from 0 to 30, preferably from 1 to 10. When m is a plural number, the B groups may be different from each other. q is an integer of from 2 to 30, preferably from 2 to 20. $R^1$ is hydrogen, an alkyl group which may be substituted, or an aromatic ring structure which may be substituted.

Specific examples of the repeating unit structure represented by the general formula (14) include unit structures described below.

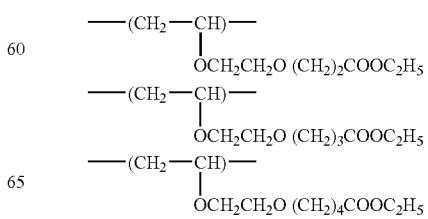

—(CH$_2$—CH)—
  |
  OCH$_2$CH$_2$O (CH$_2$)$_5$COOC$_2$H$_5$

—(CH$_2$—CH)—
  |
  OCH$_2$CH$_2$O (CH$_2$)$_6$COOC$_2$H$_5$

—(CH$_2$—CH)—
  |
  OCH$_2$CH$_2$O (CH$_2$)$_7$COOC$_2$H$_5$

—(CH$_2$—CH)—
  |
  OCH$_2$CH$_2$O (CH$_2$)$_8$COOC$_2$H$_5$

—(CH$_2$—CH)—
  |
  OCH$_2$CH$_2$O (CH$_2$)$_{10}$COOC$_2$H$_5$

—(CH$_2$—CH)—
  |
  OCH$_2$CH$_2$O (CH$_2$)$_{15}$COOC$_2$H$_5$

—(CH$_2$—CH)—
  |
  OCH$_2$CH$_2$O (CH$_2$)$_{20}$COOC$_2$H$_5$

—(CH$_2$—CH)—
  |
  OCH$_2$CH$_2$O (CH$_2$)$_2$COOCH$_3$

—(CH$_2$—CH)—
  |
  OCH$_2$CH$_2$O (CH$_2$)$_3$COOCH$_3$

—(CH$_2$—CH)—
  |
  OCH$_2$CH$_2$O (CH$_2$)$_4$COOCH$_3$

—(CH$_2$—CH)—
  |
  OCH$_2$CH$_2$O (CH$_2$)$_5$COOCH$_3$

—(CH$_2$—CH)—
  |
  OCH$_2$CH$_2$O (CH$_2$)$_6$COOCH$_3$

—(CH$_2$—CH)—
  |
  OCH$_2$CH$_2$O (CH$_2$)$_7$COOCH$_3$

—(CH$_2$—CH)—
  |
  OCH$_2$CH$_2$O (CH$_2$)$_8$COOCH$_3$

—(CH$_2$—CH)—
  |
  OCH$_2$CH$_2$O (CH$_2$)$_{10}$COOCH$_3$

—(CH$_2$—CH)—
  |
  OCH$_2$CH$_2$O (CH$_2$)$_{15}$COOCH$_3$

—(CH$_2$—CH)—
  |
  OCH$_2$CH$_2$O (CH$_2$)$_{20}$COOCH$_3$

—(CH$_2$—CH)—
  |
  O (CH$_2$CH$_2$O)$_2$ (CH$_2$)$_2$COOC$_2$H$_5$

—(CH$_2$—CH)—
  |
  O (CH$_2$CH$_2$O)$_3$ (CH$_2$)$_3$COOC$_2$H$_5$

—(CH$_2$—CH)—
  |
  O (CH$_2$CH$_2$O)$_{10}$ (CH$_2$)$_4$COOC$_2$H$_5$

—(CH$_2$—CH)—
  |
  O (CH$_2$CH$_2$O)$_{20}$ (CH$_2$)$_5$COOC$_2$H$_5$

—(CH$_2$—CH)—
  |
  O (CH$_2$CH$_2$O)$_2$ (CH$_2$)$_6$COOC$_2$H$_5$

—(CH$_2$—CH)—
  |
  O (CH$_2$CH$_2$O)$_5$ (CH$_2$)$_7$COOC$_2$H$_5$

—(CH$_2$—CH)—
  |
  O (CH$_2$CH$_2$O)$_6$ (CH$_2$)$_8$COOC$_2$H$_5$

—(CH$_2$—CH)—
  |
  O (CH$_2$CH$_2$O)$_{10}$ (CH$_2$)$_{10}$COOC$_2$H$_5$

—(CH$_2$—CH)—
  |
  O (CH$_2$CH$_2$O)$_{15}$ (CH$_2$)$_{15}$COOC$_2$H$_5$

—(CH$_2$—CH)—
  |
  O (CH$_2$CH$_2$O)$_2$(CH$_2$)$_{20}$ COOC$_2$H$_5$

—(CH$_2$—CH)—
  |
  OCH$_2$CH$_2$CH$_2$CH$_2$CH$_2$CH$_2$CH$_2$CH$_2$O (CH$_2$)$_2$COOC$_2$H$_5$

—(CH$_2$—CH)—
  |
  OCH$_2$CH$_2$CH$_2$CH$_2$O (CH$_2$)$_3$COOC$_2$H$_5$

—(CH$_2$—CH)—
  |
  OCH$_2$CH$_2$CH$_2$CH$_2$O (CH$_2$)$_4$COOC$_2$H$_5$

—(CH$_2$—CH)—
  |
  OCH$_2$CH$_2$CH$_2$CH$_2$CH$_2$CH$_2$CH$_2$CH$_2$O (CH$_2$)$_5$COOC$_2$H$_5$

—(CH$_2$—CH)—
  |
  OCH$_2$CH$_2$CH$_2$CH$_2$CH$_2$CH$_2$O (CH$_2$)$_6$COOC$_2$H$_5$

—(CH$_2$—CH)—
  |
  OCH (CH$_3$) CH$_2$O (CH$_2$)$_7$COOC$_2$H$_5$

—(CH$_2$—CH)—
  |
  OCH (CH$_3$) CH$_2$O (CH$_2$)$_8$COOC$_2$H$_5$

—(CH$_2$—CH)—
  |
  OCH$_2$CH (CH$_3$) O (CH$_2$)$_{10}$COOC$_2$H$_5$

—(CH$_2$—CH)—
  |
  OCH (C$_2$H$_5$) CH$_2$O (CH$_2$)$_{15}$COOC$_2$H$_5$

—(CH$_2$—CH)—
  |
  OCH$_2$CH (CH$_3$) O (CH$_2$)$_{20}$COOC$_2$H$_5$

—(CH$_2$—CH)—
  |
  OCH$_2$CH$_2$O (CH$_2$)$_2$COOPh

—(CH$_2$—CH)—
  |
  OCH$_2$CH$_2$O (CH$_2$)$_3$COOPh

—(CH$_2$—CH)—
  |
  OCH$_2$CH$_2$O (CH$_2$)$_4$COOPyr

—(CH$_2$—CH)—
  |
  OCH$_2$CH$_2$CH$_2$CH$_2$O (CH$_2$)$_5$COOPh

—(CH$_2$—CH)—
  |
  OCH$_2$CH$_2$O (CH$_2$)$_6$COOPh (OCH$_3$)

—(CH$_2$—CH)—
  |
  O (CH$_2$CH$_2$O)$_2$ (CH$_2$)$_7$COOPh (OCH$_3$)

—(CH$_2$—CH)—
  |
  OCH$_2$CH$_2$O (CH$_2$)$_8$COOPh (OCH$_3$)

—(CH$_2$—CH)—
  |
  OCH$_2$CH$_2$O (CH$_2$)$_{10}$COOPh (OCH$_3$)

—(CH$_2$—CH)—
  |
  OCH$_2$CH$_2$O (CH$_2$)$_{15}$COOPh (OCH$_3$)

—(CH$_2$—CH)—
  |
  OCH$_2$CH$_2$O (CH$_2$)$_{20}$COOPh (OCH$_3$)

wherein Ph is a phenyl group, and Pyr is a pyridyl group.

The polymer compound having the repeating unit structure represented by the general formula (14) can be obtained by polymerizing a polymerizable compound represented by the general formula $$CH_2=CHO(BO)_m(CH_2)_qCOOR^1 \quad (17)$$

wherein B is a linear or branched alkylene group which has 1 to 15 carbon atoms and may be substituted, m is an integer of from 1 to 30, q is an integer of from 2 to 30, and $R^1$ is hydrogen, an alkyl group which may be substituted, or an aromatic ring structure which may be substituted, with the proviso that when m is a plural number, the B groups may be different from each other.

In the general formula (17), B is a linear or branched alkylene group which has 1 to 15 carbon atoms, preferably 2 to 10 carbon atoms and may be substituted. Examples of the substituent group on the alkylene group include ethylene, propylene and butylene.

m is an integer of from 1 to 30, preferably from 1 to 10. when m is a plural number, the B groups may be different from-each other.

p is an integer of from 2 to 30, preferably from 2 to 20.

$R^1$ is hydrogen, an alkyl group which may be substituted, or an aromatic ring structure which may be substituted. The alkyl group is preferably an alkyl group having 1 to 10 carbon atoms. Examples of the aromatic ring structure include phenyl, pyridyl and biphenyl groups. Examples of the substituent group include alkyl and alkoxy groups.

Specific examples of the polymerizable compound represented by the general formula (17) include compounds described below.

$CH_2=CHOCH_2CH_2O(CH_2)_2COOC_2H_5$ $CH_2=CHOCH_2CH_2O(CH_2)_3COOC_2H_5$ $CH_2=CHOCH_2CH_2O(CH_2)_4COOC_2H_5$ $CH_2=CHOCH_2CH_2O(CH_2)_5COOC_2H_5$ $CH_2=CHOCH_2CH_2O(CH_2)_6COOC_2H_5$ $CH_2=CHOCH_2CH_2O(CH_2)_7COOC_2H_5$ $CH_2=CHOCH_2CH_2O(CH_2)_8COOC_2H_5$ $CH_2=CHOCH_2CH_2O(CH_2)_{10}COOC_2H_5$ $CH_2=CHOCH_2CH_2O(CH_2)_{15}COOC_2H_5$ $CH_2=CHOCH_2CH_2O(CH_2)20COOC_2H_5$ $CH_2=CHOCH_2CH_2O(CH_2)_2COOCH_3$ $CH_2=CHOCH_2CH_2O(CH_2)_3COOCH_3$ $CH_2=CHOCH_2CH_2O(CH_2)_4COOCH_3$ $CH_2=CHOCH_2CH_2O(CH_2)_5COOCH_3$ $CH_2=CHOCH_2CH_2O(CH_2)_6COOCH_3$ $CH_2=CHOCH_2CH_2O(CH_2)_7COOCH_3$ $CH_2=CHOCH_2CH_2O(CH_2)_8COOCH_3$ $CH_2=CHOCH_2CH_2O(CH_2)_{10}COOCH_3$ $CH_2=CHOCH_2CH_2O(CH_2)_{15}COOCH_3$ $CH_2=CHOCH_2CH_2O(CH_2)_{20}COOCH_3$ $CH_2=CHO(CH_2CH_2O)_2(CH_2)_2COOC_2H_5$ $CH_2=CHO(CH_2CH_2O)_3(CH_2)_3COOC_2H_5$ $CH_2=CHO(CH_2CH_2O)_{10}(CH_2)_4COOC_2H_5$ $CH_2=CHO(CH_2CH_2O)_{20}(CH_2)_5COOC_2H_5$ $CH_2=CHO(CH_2CH_2O)_2(CH_2)_6COOC_2H_5$ $CH_2=CHO(CH_2CH_2O)_8(CH_2)_7COOC_2H_5$ $CH_2=CHO(CH_2CH_2O)_5(CH_2)_8COOC_2H_5$ $CH_2=CHO(CH_2CH_2O)_{10}(CH_2)_{10}COOC_2H_5$ $CH_2=CHO(CH_2CH_2O)_{15}(CH_2)_{15}COOC_2H_5$ $CH_2=CHO(CH_2CH_2O)_2(CH_2)20COOC_2H_5$ $CH_2=CHOCH_2CH_2CH_2CH_2CH_2CH_2CH_2O(CH_2)_2COOC_2H_5$ $CH_2=CHOCH_2CH_2CH_2CH_2O(CH_2)_3COOC_2H_5$ $CH_2=CHOCH_2CH_2CH_2CH_2O(CH_2)_4COOC_2H_5$ $CH_2=CHOCH_2CH_2CH_2CH_2CH_2CH_2CH_2O(CH_2)_5COOC_2H_5$ $CH_2=CHOCH_2CH_2CH_2CH_2CH_2CH_2O(CH_2)_6COOC_2H_5$ $CH_2=CHOCH(CH_3)CH_2O(CH_2)_7COOC_2H_5$ $CH_2=CHOCH(CH_3)CH_2O(CH_2)_8COOC_2H_5$ $CH_2=CHOCH_2CH(CH_3)O(CH_2)_{10}COOC_2H_5$ $CH_2=CHOCH(C_2H_5)CH_2O(CH_2)_{15}COOC_2H_5$ $CH_2=CHOCH_2CH(CH_3)O(CH_2)_{20}COOC_2H_5$ $CH_2=CHOCH_2CH_2O(CH_2)_2COOPh$ $CH_2=CHOCH_2CH_2O(CH_2)_3COOPh$ $CH_2=CHOCH_2CH_2O(CH_2)_4COOPyr$ $CH_2=CHOCH_2CH_2CH_2CH_2O(CH_2)_5COOPh$ $CH_2=CHOCH_2CH_2O(CH_2)_6COOPh\ (OCH_3)$ $CH_2=CHO(CH_2CH_2O)_2\ (CH_2)_7COOPh\ (OCH_3)$ $CH_2=CHOCH_2CH_2O(CH_2)_8COOPh(OCH_3)$ $CH_2=CHOCH_2CH_2O(CH_2)_{10}COOPh(OCH_3)$ $CH_2=CHOCH_2CH_2O(CH_2)_{15}COOPh(OCH_3)$ $CH_2=CHOCH_2CH_2O(CH_2)_{20}COOPh(OCH_3)$ wherein Ph is a phenyl group, and Pyr is a pyridyl group.

Typical examples of a synthetic process of the polymerizable compound represented by the general formula (17) include those according to-such etherification process as shown by the following reaction scheme.

Reaction Scheme 14:

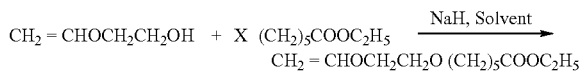
$$CH_2=CHOCH_2CH_2OH + X\,(CH_2)_5COOC_2H_5 \xrightarrow{\text{NaH, Solvent}} CH_2=CHOCH_2CH_2O\,(CH_2)_5COOC_2H_5$$

wherein X is a halogen.

The synthesis of the block polymer compound according to the present invention is often mainly performed by cationic polymerization. Examples of an initiator include combinations of a protonic acid such as hydrochloric acid, sulfuric acid, methanesulfonic acid, trifluoroacetic acid, trifluornmethanesulfonic acid or perchloric acid, of a Lewis acid such as $BF_3$, $AlCl_3$, $TiCl_4$, $SnCl_4$, $FeCl_3$, $RAlCl_2$ or $R_{1.5}AlCl_{1.5}$ (R being alkyl) and a cation source (examples of the cation source include adducts of a protonic acid, water, alcohol or vinyl ether and a carboxylic acid). Such an initiator and the polymerizable compound (monomer) represented by the general formula (17) are caused to coexist, whereby the polymerization reaction can be allowed to progress to synthesize the polymer compound.

A polymerization process preferably used in the present invention will be described. A great number of synthetic processes of a polymer containing a poly(vinyl ether) structure have been reported (for example, Japanese Patent Application Laid-Open No. 11-080221). Processes (Japanese Patent Application Laid-Open Nos. 11-322942 and 11-322866) according to cationic living polymerization by Aoshima, et al. are representative. The synthesis of the polymer is carried out by the cationic living polymerization, whereby various polymers such as a block polymer, its graft polymer and its graduation polymer can be synthesized with their lengths (molecular weight) made exactly uniform. Besides, living polymerization may also be conducted in a $HI/I_2$ or $HCl/SnCl_4$ system.

When such cationic living polymerization is conducted, it is preferred that the purity of monomers used be extremely high because a polymerization reaction is carried out at a high precision. In particular, the purity of the carboxylic acid ester type monomer represented by the general formula (17) is preferably at least 99.00%, more preferably at least 99.50%, further preferably at least 99.80%, still further preferably at least 99.90%, most preferably at least 99.95%. The purity thereof has heretofore not been fully high. In the present invention, in this respect, it has been possible to synthesize a carboxylic acid type block polymer excellent in molecular weight dispersity.

A block polymer is a copolymer having at least two block segments different in nature from each other. The so-called sequential polymerization process that polymerization of a monomer corresponding to a certain block segment is carried out, and polymerization of a monomer corresponding to a block segment different from the former block segment is subsequently conducted may be used. Alternatively, the block polymer may also be synthesized by conducting a continuous reaction of plural polymers corresponding to different block segments. The synthesis may also be carried out according to a combined process of such processes. It is preferable to use the sequential polymerization process according to living polymerization.

The polymer compound having the repeating unit structure represented by the general formula (14) is a block polymer compound. More specifically, the block polymer compound according to the present invention is a polymer compound having a block segment having the repeating unit structure represented by the general formula (14) and at least one block segment of a structure different from the above block segment.

Preferable examples of a repeating unit structure making up the block segment different from the block segment having the repeating unit structure represented by the general formula (14) include repeating unit structures represented by the general formula

$$—(CH_2—CH)— \atop |\ OR^1 \qquad (19)$$

In the general formula (19), $R^1$ is selected from a linear, branched or cyclic alkyl group having 1 to 18 carbon atoms, Ph, Pyr, Ph-Ph, Ph-Pyr, $—(CH(R^2)—CH(R^3)—O)_p—R^4$ and $—(CH_2)_m—(O)_n—R^4$, with the proviso that hydrogen in the aromatic ring may be substituted by a linear or branched alkyl group having 1 to 4 carbon atoms, and carbon in the aromatic ring may be substituted by nitrogen.

p is an integer of from 1 to 18, m is an integer of from 1 to 36, and n is 0 or 1.

$R^2$ and $R^3$ are, independently of each other, hydrogen or $CH_3$.

$R^4$ is hydrogen a linear, branched or cyclic alkyl group having 1 to 18 carbon atoms, Ph, Pyr, Ph-Ph, Ph-Pyr, $—CHO$, $—CO—CH=CH_2$, $—CO—C(CH_3)=CH_2$ or $—CH_2COOR^7$, with the proviso that when $R^4$ is any other group than hydrogen, the hydrogen bonded to the carbon may be substituted by a linear or branched alkyl group having 1 to 4 carbon atoms, F, Cl or Br, and carbon in the aromatic ring may be substituted by nitrogen.

$R^7$ is hydrogen or an alkyl group having 1 to 4 carbon atoms.

Ph is a phenyl group, and Pyr is a pyridyl group.

Further specific examples of the repeating unit structures include repeating unit structures described below.

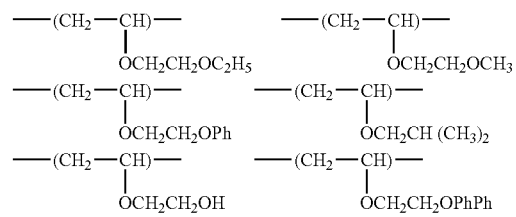

The respective segments in the block polymer compound according to the present invention may be composed of a sole repeating unit structure or a plurality of repeating unit structures. The block polymer compound according to the present invention may be a diblock polymer, triblock polymer, tetrablock polymer or a polymer composed of still more blocks, or a polymer in which such a block polymer is grafted on another polymer.

In the present invention, the content of the repeating unit structure represented by the general formula (14) contained in the polymer compound is desirably within a range of from 0.01 to 99.5 mol %, preferably from 1 to 95 mol % based on the whole polymer compound. If the content is lower than 0.01 mol %, interaction to act on the polymer may become insufficient in some cases. If the content exceeds 99.5 mol % on the other hand, the interaction acts to a too great extent to the contrary, and so function becomes insufficient in some cases. It is hence not preferable to contain this repeating unit structure in such a low or high content. The content of other unit structures than the repeating unit structure represented by the general formula (14) is desirably within a range of from 0.5 to 99.99 mol %, preferably 5 to 99 mol % based on the whole polymer compound.

The number average molecular weight (Mn) of the block polymer compound having the repeating unit structure represented by the general formula (14) is from 200 to 10,000,000, preferably from 1,000 to 1,000,000. If the molecular weight exceeds 10,000,000, intrachain and interchain entanglement of such polymer compound becomes too great, and so it is hard to be dispersed in a solvent. If the molecular weight is lower than 200, such a compound may be difficult to exhibit a steric effect as a polymer in some cases because the molecular weight is too low. The molecular weight dispersity thereof, i.e., Mw/Mn, is preferably at most 2.0, more preferably at most 1.6, further preferably at most 1.4, still further preferably at most 1.2, most preferably at most 1.1. Such a block polymer is provided as a polymer synthesized with better precision as the molecular weight dispersity is smaller. In other words, the function of each block segment is separated with better precision. Specifically, in a coloring material-containing composition, which will be described subsequently, high dispersing ability and dispersion stability can be exhibited.

In a still further aspect of the present invention, there is provided a block polymer compound having a repeating unit structure represented by the general formula

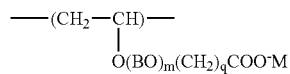
(15)

In the general formula (15), B is a linear or branched alkylene group which has 1 to 15 carbon atoms and may be substituted. m is an integer of from 1 to 30. when m is a plural number, the B groups may be different from each other. q is an integer of from 2 to 30. preferable ranges thereof are the same as those described in the general formula (14).

M is a monovalent or polyvalent metal cation. Specific examples of M include sodium, potassium and lithium as monovalent cations, and magnesium, calcium, nickel and iron as polyvalent cations. When M is a polyvalent cation, M makes a couple with COO$^-$ of the number of its valences.

A block polymer compound of the present invention having the repeating unit structure of the general formula (15) can be obtained by hydrolyzing terminal ester moieties of a polymer compound having its corresponding repeating unit structure of the general formula (14) with an alkali. The polymer compound can also be obtained by conducting hydrolysis with an acid and treating the hydrolyzed product with an alkali. However, the former process is preferred. The polymer can also be obtained by exchanging a cation after the hydrolysis with an alkali.

Specific examples of the repeating unit structure represented by the general formula (15) include unit structures described below.

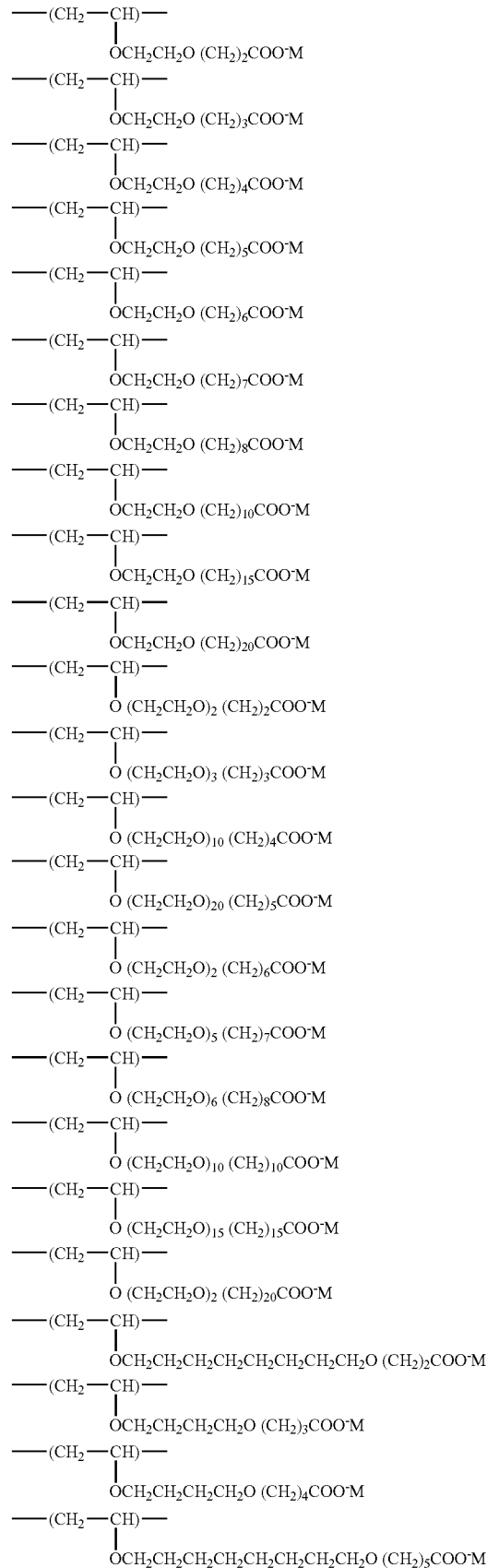

-continued

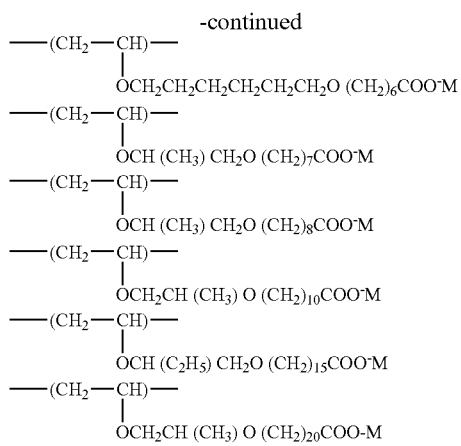

The polymer compound of the present invention having the repeating unit structure represented by the general formula (15) is a block polymer compound. More specifically, the block polymer compound according to the present invention is a polymer compound having a block segment having the repeating unit structure represented by the general formula (15) and at least one block segment of a structure different from the above block segment. Preferable examples of a repeating unit structure making up the block segment different from the block segment having the repeating unit structure represented by the general formula (15) include repeating unit structures represented by the general formula (19).

The respective segments in the block polymer compound according to the present invention may be composed of a sole repeating unit structure or a plurality of repeating unit structures. The block polymer compound according to the present invention may be a diblock polymer, triblock polymer, tetrablock polymer or a polymer composed of still more blocks, or a polymer in which such a block polymer is grafted on another polymer.

In the present invention, the content of the repeating unit structure represented by the general formula (15) contained in the polymer compound is desirably within a range of from 0.01 to 99.5 mol %, preferably from 1 to 95 mol % based on the whole polymer compound. If the content is lower than 0.01 mol %, interaction to act on the polymer may become insufficient in some cases. If the content exceeds 99.5 mol % on the other hand, the interaction acts to a too great extent to the contrary, and so function becomes insufficient in some cases. It is hence not preferable to contain this repeating unit structure in such a low or high content. The content of other unit structures than the repeating unit structure represented by the general formula (15) is desirably within a range of from 0.5 to 99.99 mol %, preferably 5 to 99 mol % based on the whole polymer compound.

The number average molecular weight (Mn) of the block polymer compound having the repeating unit structure represented by the general formula (15) is from 200 to 10,000,000, preferably from 1,000 to 1,000,000. If the molecular weight exceeds 10,000,000, intrachain and interchain entanglement of such polymer compound becomes too great, and so it is hard to be dispersed in a solvent. If the molecular weight is lower than 200, such a compound may be difficult to exhibit a steric effect as a polymer in some cases because the molecular weight is too low. The molecular weight dispersity thereof, i.e., Mw/Mn, is preferably at most 2.0, more preferably at most 1.6, further preferably at most 1.4, still further preferably at most 1.2, most preferably at most 1.1. The function of each block segment is separated with better precision as the molecular weight dispersity is smaller as described above. Specifically, in a coloring material-containing composition, which will be described subsequently, high dispersing ability and dispersion stability can be exhibited.

Preferable properties of the block polymer compound having the repeating unit structure represented by the general formula (14) or (15) include an amphipatic property. Such block polymer compounds have both hydrophobic block segment and hydrophilic block segment and so can exhibit the amphipatic property. When the block polymer compound according to the present invention is amphipatic, it can form a micelle state in a hydrophilic solvent. In this case, preferable properties can be exhibited in a recording material which will be described subsequently.

In order to improve dispersion stability and clathrate property, it is preferable that the molecular motion property of a block polymer be more flexible in that such a bloc polymer is physically entangled with the surface of a functional material and is liable to have affinity for it. The fact that the molecular motion property is flexible is preferred in that it is easy to form a coating layer on a recording medium, as will be described in detail subsequently. In order for the block polymer to have such property, the glass transition temperature Tg of a main chain of the block polymer is preferably at most 20° C., more preferably at most 0° C., further preferably at most −20° C. In this respect also, the polymer having the poly(vinyl ether) structure is preferably used because it generally has a low glass transition temperature and flexible properties. In the case of the repeating unit structures exemplified above, the glass transition temperatures of most of them are about −20° C. or lower.

In a yet still further aspect of the present invention, there is provided a block polymer composition comprising a block polymer compound having the repeating unit structure represented by the general formula (14) or (15).

The composition according to the present invention comprises the block polymer compound described above, a coloring material and a functional material exhibiting a useful prescribed function. The block polymer compound may preferably be used for satisfactorily dispersing the coloring material, functional material and the like. The coloring material and functional material are preferably liquid or solid, or may also be soluble materials. For example, oil, pigments, metals, herbicides, insecticides, biomaterials, medicines, dyes, molecular catalysts, etc. may also be used.

In a yet still further aspect of the present invention, there is provided a composition comprising a block polymer composed of a poly(vinyl ether) repeating unit structure containing an aliphatic carboxylic acid ester, an aliphatic carboxylic acid or an aliphatic carboxylic acid salt therein, a solvent or dispersion medium and a coloring material. Examples of the repeating unit structure containing an aliphatic carboxylic acid ester, an aliphatic carboxylic acid or an aliphatic carboxylic acid salt therein include those represented by the general formula (14) or (15). However, other structures may also be included.

Examples thereof include:

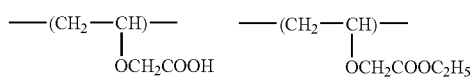

-continued

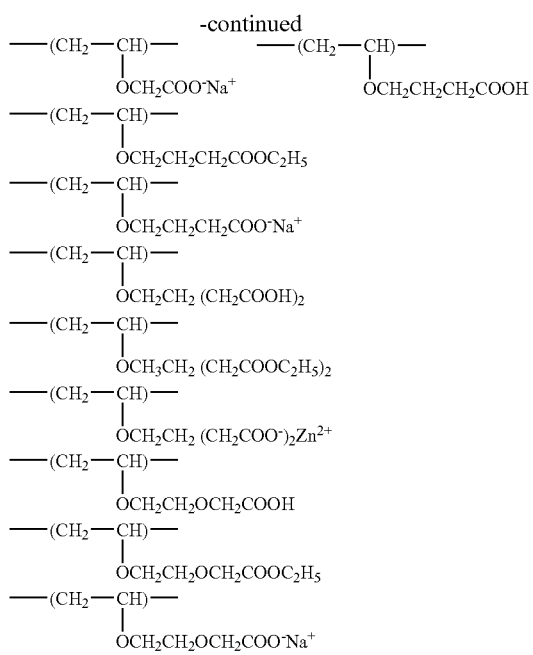

In a yet still further aspect of the present invention, there is provided a composition comprising a polymer compound having at least one selected from repeating unit structures represented by general formulae

wherein B is a linear or branched alkylene group which has 1 to 15 carbon atoms and may be substituted, m is an integer of from 1 to 30, t is an integer of from 1 to 30, and $R^1$ is hydrogen, an alkyl group which may be substituted, or an aromatic ring structure which may be substituted, with the proviso that when m is a plural number, the B groups may be different from each other, and

wherein B is a linear or branched alkylene group which has 1 to 15 carbon atoms and may be substituted, m is an integer of from 1 to 30, t is an integer of from 1 to 30, and M is a monovalent or polyvalent metal cation, with the proviso that when m is a plural number, the B groups may be different from each other.

In the general formulae (12) and (13), t is at least 1, preferably at least 2, more preferably at least 4.

The number average molecular weight of the polymer compound having at least one selected from the repeating unit structures represented by the general formulae (12) and (13) is from 200 to 10,000,000, preferably from 1,000 to 1,000,000. If the molecular weight exceeds 10,000,000, intrachain and interchain entanglement of such polymer compound becomes too great, and so it is hard to be dispersed in a solvent. If the molecular weight is lower than 200, such a compound may be difficult to exhibit a steric effect as a polymer in some cases because the molecular weight is too low.

The composition according to the present invention comprises the polymer compound described above, a coloring material and a functional material exhibiting a useful prescribed function. The polymer compound may preferably be used for satisfactorily dispersing the coloring material, functional material and the like. The coloring material and functional material are preferably particulate solids. As the particulate solid, may be used a pigment, metal, herbicide, insecticide or biomaterial, for example, a medicine.

The content of the particulate solid used in the composition according to the present invention is preferably 0.1 to 50% by weight based on the weight of the composition according to the present invention. The particulate solid may also be a soluble material, and a dye or molecular catalyst may also be used.

The content of the functional material used in the composition according to the present invention is preferably 0.01 to 90% by weight, more preferably 0.1 to 50% by weight based on the weight of-the composition according to the present invention.

The content of the block polymer compound having the repeating unit structure represented by the general formula (14) or (15) contained in the composition according to the present invention is 0.2 to 99% by weight, preferably 0.5 to 70% by weight based on the weight of the composition. In the block polymer compound having the repeating unit structure containing an aliphatic carboxylic acid ester, an aliphatic carboxylic acid or an aliphatic carboxylic acid salt therein, the content thereof is equivalent to that described above. The same shall apply hereinafter with respect to the content of the block polymer compound.

Examples of the composition according to the present invention include recording materials comprising a solvent or dispersion medium, a coloring material and the polymer compound having at least one selected from the repeating unit structures represented by the general formulae (12) and (13).

Other examples of the composition according to the present invention include recording materials comprising a solvent or dispersion medium, a binder, a coloring material and the polymer compound having the repeating unit structure represented by the general formulae (14) or (15). Specific examples of the recording materials include toner compositions comprising a dispersion medium such as a binder resin, a coloring material and the block polymer compound having the repeating unit structure represented by the general formulae (14) or (15).

Other specific examples of the recording materials include toner compositions comprising a dispersion medium such as a binder resin, a coloring material and the polymer compound having at least one selected from the repeating unit structures represented by the general formulae (12) and (13).

Further specific examples of the recording materials include ink compositions comprising a solvent, a coloring material and the polymer compound having at least one selected from the repeating unit structures represented by the general formulae (12) and (13). Still further specific examples of the recording materials include ink compositions comprising a solvent, a coloring material and the block polymer compound having the repeating unit structure represented by the general formulae (14) or (15).

The ink compositions according to the present invention will hereinafter be described.

The content of the polymer compound having at least one selected from the repeating unit structures represented by the general formulae (12) and (13) or the block polymer compound having the repeating unit structure represented by the general formulae (14) or (15) is within a range of from 0.1 to 90% by weight, preferably from 1 to 80% by weight. The polymer compound is preferably used in a proportion of from 1 to 30% by weight for ink-jet printer.

Other components than the polymer compound contained in the ink compositions according to the present invention will hereinafter be described in detail. Other components include water, a hydrophilic solvent, a coloring material and additives.

[Water]

Water used in the present invention is preferably ion-exchanged water from which metal ions or the like have been removed, pure water or ultrapure water.

[Hydrophilic Solvent]

As the hydrophilic solvent, may be used, for example, a polyhydric alcohol such as ethylene glycol, diethylene glycol, triethylene glycol, polyethylene glycol, propylene glycol, polypropylene glycol or glycerol, a polyhydric alcohol ether such as ethylene glycol monomethyl ether, ethylene glycol monoethyl ether, ethylene glycol monobutyl ether, diethylene glycol monoethyl ether or diethylene glycol monobutyl ether, or a nitrogen-containing solvent such as N-methyl-2-pyrrolidone, substituted pyrrolidone or triethanolamine. A monohydric alcohol such as methanol, ethanol or isopropyl alcohol may also be used for the purpose of facilitating drying of an aqueous dispersion on a recording medium.

The content of water and the hydrophilic solvent-used in the ink compositions according to the present invention is preferably within a range of from 20 to 95% by weight, more preferably from 30 to 90% by weight based on the weight of each ink composition.

[Coloring Material]

In the ink compositions according to the present invention, a coloring material such as a pigment or dye is contained. A pigment is preferably used in the present invention.

Specific examples of pigments and dyes used in the ink compositions according to the present invention will hereinafter be described.

The pigments may be either organic pigment or inorganic pigments, and black pigments and pigments of three primary colors of cyan, magenta and yellow may preferably be used in the ink compositions. Other pigments than those described above, colorless or light-colored pigments, metalescent pigments and the like may also be used. Pigments newly synthesized for the present invention may also be used.

Examples of commercially available black, cyan, magenta and yellow pigments are mentioned below.

As examples of black pigments, may be mentioned Raven 1060, Raven 1080, Raven 1170, Raven 1200, Raven 1250, Raven 1255, Raven 1500, Raven 2000, Raven 3500, Raven 5250, Raven 5750, Raven 7000, Raven 5000 ULTRAII, Raven 1190 ULTRAII (products of Columbian Carbon Co.), Black Pearls L, MOGUL-L, Regal 400R, Regal 660R, Regal 330R, Monarch 800, Monarch 880, Monarch 900, Monarch 1000, Monarch 1300 and Monarch 1400 (all, products of Cabot Co.), Color Black FW1, Color Black FW2, Color Black FW200, Color Black 18, Color Black S160, Color Black S170, Special Black 4, Special Black 4A, Special Black 6, Printex 35, Printex U, Printex 140U, Printex V and Printex 140V (all, products of Degussa Co.), and No. 25, No. 33, No. 40, No. 47, No. 52, No. 900, No. 2300, MCF-88, MA 600, MA 7, MA 8 and MA 100 (all, products of Mitsubishi Kagaku Co., Ltd.). However, black pigments are not limited thereto.

As examples of cyan pigments, may be mentioned C.I. Pigment Blue-1, C.I. Pigment Blue-2, C.I. Pigment Blue-3, C.I. Pigment Blue-15, C.I. Pigment Blue-15:2, C.I. Pigment Blue-15:3, C.I. Pigment Blue-15:4, C.I. Pigment Blue 16, C.I. Pigment Blue 22 and C.I. Pigment Blue-60. However, cyan pigments are not limited thereto.

As examples of magenta pigments, may be mentioned C.I. Pigment Red-5, C.I. Pigment Red-7, C.I. Pigment Red-12, C.I. Pigment Red-48, C.I. Pigment Red-48:1, C.I. Pigment Red-57, C.I. Pigment Red-112, C.I. Pigment Red-122, C.I. Pigment Red-123, C.I. Pigment Red-146, C.I. Pigment Red-168, C.I. Pigment Red-184, C.I. Pigment Red-202 and C.I. Pigment Red-207. However, magenta pigments are not limited thereto.

As examples of yellow pigments, may be mentioned C.I. Pigment Yellow-12, C.I. Pigment Yellow-13, C.I. Pigment Yellow-14, C.I. Pigment Yellow-16, C.I. Pigment Yellow-17, C.I. Pigment Yellow-74, C.I. Pigment Yellow-83, C.I. Pigment Yellow-93, C.I. Pigment Yellow-95, C.I. Pigment Yellow-97, C.I. Pigment Yellow-98, C.I. Pigment Yellow-114, C.I. Pigment Yellow-128, C.I. Pigment Yellow-129, C.I. Pigment Yellow-151 and C.I. Pigment Yellow 154. However, yellow pigments are not limited thereto.

Pigments self-dispersing in water may also be used in the compositions according to the present invention. Examples of the self-dispersing pigment include those making good use of a steric hindrance effect with a polymer adsorbed on the surface of a pigment and those making good used of electrostatic repulsion force. Commercially available products thereof include CAB-O-JET 200 and CAB-O-JET 300 (both, products of Cabot Co.), and Microjet Black CW-1 (product of Orient Chemical Industries Ltd.).

The pigments used in the ink compositions according to the present invention are preferably used in a proportion of from 0.1 to 50% by weight based on the weight of each ink composition. If the proportion thereof is lower than 0.1% by weight, the optical density of an image formed by such an ink composition becomes insufficient. If the proportion exceeds 50% by weight, the fixing ability of an image formed may be deteriorated in some cases. Preferable range thereof is from 0.5% by weight to 30% by weight.

Dyes may also be used in the ink compositions according to the present invention. Such water-soluble direct dyes, acid dyes, basic dyes, reactive dyes and food colors as described below, or insoluble colors such as dispersion dyes may also be used.

Examples of the water-soluble dyes include:

direct dyes such as C.I. Direct Black-17, -19, -22, -32, -38, -51, -62, -71, -108, -146 and -154; C.I. Direct Yellow-12, -24, -26, -44, -86, -87, -100, -130 and -142; C.I. Direct Red-1, -4, -13, -17, -23, -28, -31, -62, -79, -81, -83, -89, -227, -240, -242 and -243; C.I. Direct Blue-6, -22, -25, -71, -78, -86, -90, -106 and -199; C.I. Direct Orange-34, -39, -44, -46 and -60; C.I. Direct Violet-47 and -48; C.I. Direct Brown-109; and C.I. Direct Green-59;

acid dyes such as C.I. Acid Black-2, -7, -24, -26, -31, -52, -63, -112, -118, -168, -172 and -208; C.I. Acid Yellow-11, -17, -23, -25, -29, -42, -49, -61 and -71; C.I. Acid Red-1, -6, -8, -32, -37, -51, -52, -80, -85, -87, -92, -94, -115, -180, -254, -256, -289, -315 and -317; C.I. Acid Blue-9, -22, -40, -59, -93, -102, -104, -113, -117, -120, -167, -229, -234 and -254; C.I. Acid Orange-7 and -19; and C.I. Acid Violet-499;

reactive dyes such as C.I. Reactive Black-1, -5, -8, -13, -14, -23, -31, -34 and -39; C.I. Reactive Yellow-2, -3, -13, -15, -17, -18, -23, -24, -37, -42, -57, -58, -64, -75, -76, -77, -79, -81, -84, -85, -87, -88, -91, -92, -93, -95, -102, -111, -115, -116, -130, -131, -132, -133, -135, -137, -139, -140, -142, -143, -144, -145, -146, -147, -148, -151, -162 and -163; C.I. Reactive Red-3, -13, -16, -21, -22, -23, -24, -29, -31, -33, -35, -45, -49, -55, -63, -85, -106, -109, -111, -112, -113, -114, -118, -126, -128, -130, -131, -141, -151, -170, -171, -174, -176, -177, -183, -184, -186, -187, -188, -190, -193, -194, -195, -196, -200, -201, -202, -204, -206, -218 and -221; C.I. Reactive Blue-2, -3, -5, -8, -10, -13, -14, -15, -18, -19, -21, -25, -27, -28, -38, -39, -40, -41, -49, -52, -63, -71, -72, -74, -75, -77, -78, -79, -89, -100, -101, -104, -105, -119, -122, -147, -158, -160, -162, -166, -169, -170, -171, -172, -173, -174, -176, -179, -184, -190, -191, -194, -195, -198, -204, -211, -216 and -217; C.I. Reactive Orange-5, -7, -11, -12, -13, -15, -16, -35, -45, -56, -62, -70, -72, -74, -82, -84, -87, -91, -92, -93, -95, -97 and -99; C.I. Reactive Violet-1, -4, -5, -6, -22, -24, -33, -36 and -38; C.I. Reactive Green-5, -8, -12, -15, -19 and -23; and C.I. Reactive Brown-2, -7, -8, -9, -11, -16, -17, -18, -21, -24, -26, -31, -32 and -33;

basic dyes such as C.I. Basic Black-2; C.I. Basic Red-1, -2, -9, -12, -13, -14 and -27; C.I. Basic Blue-1, -3, -5, -7, -9, -24, -25, -26, -28 and -29; and C.I. Basic Violet-7, -14 and -27; and food colors such as C.I. Food Black-1 and -2.

The above-exemplified coloring materials are preferred for the inks according to the present invention. However, the coloring materials used in the ink compositions according to the present invention are not limited to the above-described coloring materials. The dyes used in the ink compositions according to the present invention are preferably used in a proportion of from 0.1 to 50% by weight based on the weight of each ink composition.

[Additives]

Various additives and auxiliaries may be added to the compositions according to the present invention as needed. One of the additives is a dispersion stabilizer for stably dispersing a pigment in a solvent. The compositions according to the present invention have a function of dispersing a particulate solid such as a pigment by virtue of a polymer having the poly(vinyl ether) structure. However, another dispersion stabilizer may be added when dispersion is insufficient.

As another dispersion stabilizer, may be used a resin having both hydrophilic and hydrophobic moieties or a surfactant. Examples of the resin having both hydrophilic and hydrophobic moieties include copolymers of a hydrophilic monomer and a hydrophobic monomer.

Examples of the hydrophilic monomer include acrylic acid, methacrylic acid, maleic acid, fumaric acid, monoesters of the above carboxylic acids, vinylsulfonic acid, styrenesulfonic acid, vinyl alcohol, acrylamide and methacryloxyethyl phosphate, and examples of the hydrophobic monomer include styrene, styrene derivatives such as α-methylstyrene, vinylcyclohexane, vinylnaphthalene derivatives, acrylic acid esters and methacrylic acid esters. The copolymer used may be any of a random copolymer, a block copolymer and a graft copolymer. It goes without saying that both hydrophilic and hydrophobic monomers are not limited to those described above.

As the surfactant, may be used an anionic, nonionic, cationic or amphoteric surfactant. Examples of the anionic surfactant include fatty acid salts, alkylsulfate salts, alkylarylsulfonic acid salts, alkyldiaryl ether disulfonic acid salts, dialkylsulfosuccinic acid salts, alkylphosphoric acid salts, naphthalenesulfonic acid-formalin condensates, polyoxyethylene alkylphosphate salts and glycerol borate fatty acid esters. Examples of the nonionic surfactant include polyoxyethylene alkyl ethers, polyoxyethylene oxypropylene block copolymers, sorbitan fatty acid esters, glycerol fatty acid esters, polyoxyethylene fatty acid esters, polyoxyethylene alkylamines, fluorine-containing surfactants and silicon-containing surfactants. Examples of the cationic surfactant include alkylamine salts, quaternary ammonium salts, alkylpyridinium salts and alkylimidazolium salts. Examples of the amphoteric surfactant include alkylbetaine, alkylamine oxides and phosphatidyl choline. The surfactants are also not limited to those described above.

A hydrophilic solvent may be additionally added to the compositions according to the present invention. When such a composition is used in ink-jet in particular, the hydrophilic solvent is used for the purpose of preventing the drying and crusting of an ink at a nozzle part. Such hydrophilic solvents may be used either singly or in any combination thereof. As the hydrophilic solvents, may be mentioned those described above. When the hydrophilic solvents are used in an ink, the content thereof is within a range of from 0.1 to 60% by weight, preferably from 1 to 25% by weight based on the weight of the ink.

As other additives in the case where the composition is used as an ink, may also be added a pH adjustor for achieving the stability of the ink and the stability of the ink in a recording apparatus with a piping, a penetrant for facilitating the penetration of the ink to speed up the apparent drying thereof, a mildew-proofing agent for preventing the occurrence of mildew in the ink, a chelating agent for scavenging metal ions in the ink to prevent deposition of metals at a nozzle part and of insoluble matter in the ink, an anti-foaming agent for preventing the occurrence of bubbles in circulation, movement or production of the ink, an antioxidant, a viscosity modifier, a conductivity-imparting agent, an ultraviolet absorbent, etc.

An ink composition according to the present invention can be prepared by mixing the above-described components into a uniform solution or dispersion. For example, plural components are mixed, and ground and dispersed by means of a sand mill, ball mill, homogenizer or the like to make an ink mother liquor, and solvent(s) and additive(s) are added thereto to adjust the physical properties thereof, thereby preparing an ink composition.

A toner composition according to the present invention will hereinafter be described. Specifically, the toner compositions comprise a dispersion medium such as a binder resin, a coloring material and the polymer compound having at least one selected from the repeating unit structures represented by the general formulae (12) and (13).

Another toner composition according to the present invention will hereinafter be described. Specifically, the toner compositions comprise a dispersion medium such as a binder resin, a coloring material and the polymer compound having the repeating unit structure represented by the general formula (1) or (2).

The content of the polymer compound having at least one selected from the repeating unit structures represented by the general formulae (1) or (2) contained in the toner composition according to the present invention is within a range of from 0.1 to 50% by weight, preferably from 0.5 to 30% by weight.

The content of the polymer compound having the repeating unit structure represented by the general formula (1) or (2) contained in the toner composition according to the present invention is within a range of from 0.1 to 50% by weight, preferably from 0.5 to 30% by weight.

The polymer compound according to the present invention may also be used as a binder resin itself or together with a binder resin such as a styrene-acrylic resin or polyester resin.

Other components than the polymer compound contained in the toner compositions according to the present invention will hereinafter be described in detail. Other components include a binder resin, a coloring material (pigment or dye), a charge-control agent, a parting agent, external additives, magnetic particles, etc.

Examples of the binder resin include styrene-acrylic copolymers, polyester and polycarbonate. The content of the binder resin used is preferably from 10 to 99% by weight. As the coloring material, may be used any of the pigments and dyes mentioned in the description of the ink compositions. The content of the coloring material used is preferably from 0.1 to 50% by weight. Examples of the charge-control agent include metal-azo complexes, triphenylmethane dyes, Nigrosine and ammonium salts. The content of the charge control agent used is preferably from 0.1 to 30% by weight. Examples of the parting agent include synthetic waxes and natural waxes. Examples of the external additives include inorganic fine particles such as silica, alumina and titania, and fine particles of resins such as polyvinylidene fluoride (PVDF) and polytetrafluoroethylene. Examples of the magnetic particles include magnetite, hematite and ferrite. The toner compositions may function when all the component described above are not always contained, or may contain other components than those described above.

A toner composition according to the present invention can be prepared in accordance with, for example, the following process. The above-described components are mixed and melt-kneaded into a uniform mixture, the resulting mixture is then ground by a Speed mill or Jet mill, and the resultant ground product is classified to obtain a toner having a desired size. The external additive is added to the toner, and the mixture is mixed by a mixer, whereby the toner composition can be prepared. The compositions according to the present invention described above are used as various compositions in addition to the ink compositions and toner compositions. In the case of a composition containing a coloring material, however, the coloring material is preferably enclosed with the block polymer compound according to the aspect of the present invention, typically, in that deterioration of the weather resistance of the coloring material is prevented. In the case of a water-based ink, an oil-soluble coloring material or coloring material particles on a hydrophobic surface can be comparatively simply enclosed with a micelle formed by the block polymer compound. A method of thickening the compositions according to the aspects of the present invention will hereinafter be described. This method is a method of thickening the compositions by bringing a hydrogen ion or metal cation into contact with such a composition. This method typically comprises bringing a hydrogen ion or polyvalent metal cation (for example, cation of zinc, aluminum, calcium, barium, nickel or the like) into contact with a composition having the block polymer compound, by which a micelle has been formed in an aqueous solution, and a functional material, thereby aggregating micelle particles to thicken the composition. Since the block polymer compound is such that a carboxylic acid salt or the like is ionized, the ionic functional group is neutralized by, for example, bringing a sufficient amount of the hydrogen ion or metal cation into contact therewith, thereby rapidly increase affinity between micelles, and at the same time greatly increase viscosity. A preferable application example of this method is an ink composition. The ink composition according to the present invention is preferably applied to an image forming method and image forming apparatus which will be described subsequently.

The compositions according to the present invention may have responsiveness to irritation. It is also possible to impart good fixing ability to an ink composition by thickening the ink composition by virtue of the irritation responsiveness by irritating the composition in the course of formation of an image. As the irritation, that suitable for forming an image is selected from among temperature change, exposure to electromagnetic wave, pH change, concentration change, etc., and combinations thereof.

The image forming method and image forming apparatus using the ink composition according to the present invention will hereinafter be described.

[Image Forming Method and Image Forming Apparatus]

The ink compositions according to the present invention can be used in various image forming methods and apparatus by various kinds of printing systems, ink-jet systems and electrophotographic systems, and an image can be formed by an image forming method using such an apparatus.

The image forming method according to the present invention is a method of forming an excellent image with the compositions according to the present invention. The image forming method according to the present invention is preferably an image forming method by ejecting an ink composition according to the present invention from an ink ejecting part to apply it on to a recording medium, thereby conducting recording. In the formation of the image, is preferably used a method using an ink-jet system that thermal energy is applied to an ink to eject the ink.

As an ink-jet printer using the ink composition for ink-jet according to the present invention, may be applied various ink-jet recording apparatus of a piezo-ink-jet system using a piezoelectric element, a thermal ink-jet system that thermal energy is applied to an ink to form bubbles in the ink, thereby conducting recording, and the like.

The ink-jet recording apparatus will hereinafter be schematically described with reference to FIG. 1. However, the apparatus shown in FIG. 1 is strictly an example of the construction, and does not limit the present invention.

FIG. 1 is a block diagram illustrating the construction of the ink-jet recording apparatus. In FIG. 1, to CPU 50 are connected an X-direction drive motor 56 for driving a head 70 in an X-direction and a Y-motor drive motor 58 for driving the head 70 in a Y-direction through an X-motor drive circuit 52 and a Y-motor drive circuit 54, respectively. The X-direction drive motor 56 and the Y-motor drive motor 58 are driven through the X-motor drive circuit 52 and the Y-motor drive circuit 54, respectively, according to indication of CPU, thereby determining a position of the head 70 to a recording medium.

As illustrated in FIG. 1, a head drive motor 60 is connected to the head 70 in addition to the X-direction drive motor 56 and the Y-motor drive motor 58, CPU 50 controls the head drive motor 60 to conduct the drive of the head 70, i.e., ejection of an ink-jet ink. Both X-encoder 62 and Y-encoder 64 for detecting the position of the head are connected to CPU 50 to input positional information of the head 70. A control program is also inputted in a program memory 66. CPU 50 moves the head 70 on the basis of this control program and the positional information from the X-encoder 62 and Y-encoder 64 to arrange the head at a desired position on the recording medium so as to eject the ink-jet ink. In such a manner, a desired image can be formed on the recording medium. In the case of an image forming apparatus, in which plural ink-jet inks can be charged, a desired image can be formed on a recording medium by conducting such process as described above with the respective ink-jet inks the prescribed number of times.

After the ink-jet ink is ejected, as needed, the head 70 may be moved to a position where a removing means (not illustrated) for removing excessive ink attached to the head is arranged, to clean up the head 70 by wiping or the like. As a specific method for cleaning, the conventional method may be used as it is.

After completion of the formation of the image, the recording medium, on which the image has been formed, is replaced by a new recording medium by means of a recording medium-conveying mechanism (not illustrated).

In the present invention, the above-described embodiment can be modified or changed within limits not departing from the subject matter of the invention. For example, the embodiment that the head 70 is moved in both X- and Y-directions has been described above. However, the head 70 may be moved only in the X-direction (or Y-direction), and the recording medium may be moved in the Y-direction (or X-direction), thereby forming an image while interlocking these movements.

According to the present invention, a head equipped with a means (for example, electrothermal converter or laser beam) for generating thermal energy as energy used for ejection of an ink-jet ink and ejecting the ink-jet ink by the thermal energy brings about an excellent effect. According to such system, the formation of a high-definition image can be achieved. The formation of a far excellent image can be achieved by using the ink compositions for ink-jet according to the present invention.

With respect to the typical construction and principle of the apparatus equipped with the means for generating thermal energy, those using the basic principle disclosed in, for example, U.S. Pat. Nos. 4,723,129 and 4,740,796 are preferred. This system may be applied to any of the so-called On-Demand type and continuous type. In particular, the On-Demand type is effective because at least one driving signal which corresponds to recording information and gives a rapid temperature rise exceeding nuclear boiling is applied to an electrothermal converter arranged corresponding to a liquid path, in which a liquid (ink) is retained, thereby causing the electrothermal converter to generate thermal energy to cause film boiling on the heat-acting surface of a recording head, so that a bubble can be formed in the liquid in response to the driving signal in relation of one to one. The liquid is ejected through an ejection opening by the growth-contraction of this bubble to form at least one droplet. When the driving signal is applied in the form of a pulse, the growth-contraction of the bubble is suitably conducted in a moment, so that the ejection of the liquid excellent in responsiveness in particular can be achieved. It is therefore preferable to use such pulsed signals. As the pulsed driving signal, such signals as described in U.S. Pat. Nos. 4,463,359 and 4,345,262 are suitable. When the conditions described in U.S. Pat. No. 4,313,124 that is an invention relating to the rate of temperature rise on the heat-acting surface are adopted, far excellent ejection can be conducted.

As the construction of the head, such combined constructions (linear liquid flow path or perpendicular liquid flow path) of ejection openings, a liquid flow path and electrothermal converters as disclosed in the above-described publications, and besides constructions based on U.S. Pat. Nos. 4,558,333 and 4,459,600 which disclose the construction that a heat-acting portion is arranged in a curved region may also be included in the present invention. Constructions based on Japanese Patent Application Laid-Open,No. 59-123670 which discloses the construction that a slit common to a plurality of electrothermal converters are used as an ejection part of the electrothermal converters, and Japanese Patent Application Laid-Open No. 59-138461 which discloses the construction that an opening absorbing pressure wave of thermal energy is provided in opposition to an ejection part may also be effective for the present invention. In other words, ejection of the ink-jet ink can be efficiently performed with certainty according to the present invention even when the type of the head is any type.

Further, in the image forming apparatus according to the present invention, the present invention can be effectively applied to a full-line type recording head having a length corresponding to the longest width of recording media. Such a head may be either the construction that the length is met by a combination of plural recording heads or the construction as one recording head integrally formed.

In addition, the present invention is effective even in a serial type so far as a head is fixed to an apparatus body or even when a replaceable, chip type head, in which electrical connection to an apparatus body and the feed of an ink from the apparatus body become feasible by installing the head in the apparatus body, is used.

Further, the apparatus may additionally have a droplet removing means. When such a means is added, a far excellent ejecting effect can be realized.

Besides, addition of preliminary auxiliary means and the like which are provided as constitution of the recording apparatus according to the present invention is preferred because the effects of the present invention can be more stabilized. As specific examples thereof, may be mentioned capping means for the head, pressurizing or sucking means, preliminary heating means for conducting heating by using electrothermal converters, other heating elements than these or combinations thereof, and preliminary ejecting means for conducting ejection separate from ejection of an ink.

In the present invention, the above-described film boiling system is most effective for the above-described ink compositions.

The amount of an ink-jet ink ejected from each ejection orifice of the ejection head in the apparatus according to the present invention is preferably within a range of from 0.1 to 100 picoliters.

The ink compositions according to the present invention may also be used in indirect recording apparatus using such a recording system that an ink is applied to an intermediate transfer member, and the applied ink is then transferred to a recording medium such as paper, or the like. Further, the ink compositions may also be applied to apparatus making good use of an intermediate transfer member by a direct recording system.

The present invention will hereinafter be described in detail by the following Examples. However, the present invention is not limited to these examples.

EXAMPLE 1

<Synthesis of $CH_2=CHOCH_2CH_2O(CH_2)_6COOC_2H_5$>

2-Hydroxyethyl vinyl ether (0.42 mol) was added dropwise to a flask, in which sodium hydride (0.42 mol) had been dispersed in anhydrous toluene (60 ml), under a nitrogen atmosphere. After the drop addition, ethyl 7-bromoheptanoate (0.42 mol) was added dropwise. Thereafter, tetrabutylammonium iodide (2 g) was immediately added to stir the mixture at 100° C. for 3 hours. The reaction mixture was poured into water, and the resultant-organic layer was washed with water and then combined with an extract from ether. The combined layer was dried over anhydrous sodium sulfate. After the solvent was removed, the resultant residue was distilled under reduced pressure to obtain 52 g of $CH_2=CHOCH_2CH_2O(CH_2)_6COOC_2H_5$ (yield: 50.7%).

EXAMPLE 2

Synthesis of Polymer Compound:

$CH_2=CHOCH_2CH_2O(CH_2)_6COOC_2H_5$ (0.1 mol) obtained in EXAMPLE 1, water (0.001 mol) and ethylaluminum dichloride (0.005 mol) were subjected to cationic polymerization in anhydrous toluene.

The reaction was completed after 20 hours, methylene chloride and water were added, the resultant mixture was washed with water, diluted hydrochloric acid and alkali in that order and then dried over anhydrous sodium sulfate, and the solvent was distilled off to obtain a polymer compound. The number average molecular weight of the polymer compound by excluded volume chromatography was 3,200.

EXAMPLE 3

<Synthesis of $CH_2=CHOCH_2CH_2O(CH_2)_5COOC_2H_5$>

Synthesis was carried out in the same manner as in EXAMPLE 1 except that ethyl 7-bromoheptanoate was changed to ethyl 6-bromohexanoate, thereby obtaining $CH_2=CHOCH_2CH_2O(CH_2)_5COOC_2H_5$ (yield: 41%).

EXAMPLE 4

Polymeization was conducted in the same manner as in EXAMPLE 2 except that $CH_2=CHOCH_2CH_2O(CH_2)_5COOC_2H_5$ obtained in EXAMPLE 3 was used, thereby obtaining a polymer compound. The number average molecular weight of the polymer compound by excluded volume chromatography was 1,800.

EXAMPLE 5

The polymer compound synthesized in EXAMPLE 2 was stirred together with a 5N aqueous solution of sodium hydroxide for 40 hours at room temperature (23° C.) to hydrolyze the ester. The reaction mixture was neutralized with 5N hydrochloric acid and extracted with methylene chloride. After the resultant extract was dried, the solvent was distilled off to obtain a free carboxylic acid type polymer. The polymer was neutralized with an equiamount of 1N sodium hydroxide, and water was distilled off to obtain a sodium salt type carboxylate polymer compound.

EXAMPLE 6

Three parts by weight of a pigment (MOGUL-L, trade name; product of Cabot Co.), 5 parts by weight of the polymer compound obtained in EXAMPLE 2 and 15 parts by weight of diethylene glycol were added to 77 parts by weight of ion-exchanged water and dispersed therein by means of an ultrasonic homogenizer. The resultant dispersion was filtered under pressure through a filter having a pore size of 1 μm to prepare an ink composition. The dispersibility of the pigment was good.

EXAMPLE 7

Three parts by weight of a pigment (MOGUL-L, trade name; product of Cabot Co.), 3 parts by weight of the sodium salt type carboxylate polymer compound obtained in EXAMPLE 5 and 15 parts by weight of diethylene glycol were added to 79 parts by weight of ion-exchanged water and dispersed therein by means of an ultrasonic homogenizer. The resultant dispersion was filtered under pressure through a filter having a pore size of 1 μm to prepare an ink composition. The dispersibility of the pigment was good.

EXAMPLE 8

The ink composition prepared in EXAMPLE 6 was used to conduct ink-jet recording. The ink composition obtained in EXAMPLE 6 was charged into an ink tank of a Bubble Jet (trademark) printer (BJF800, trade name; manufactured by Canon Inc.) to conduct recording on plain paper by means of the ink-jet printer. As a result, a beautiful black print was obtained.

EXAMPLE 9

The ink composition prepared in EXAMPLE 7 was used to conduct ink-jet recording. The ink composition obtained in EXAMPLE 7 was charged into an ink tank of a Bubble Jet (trademark) printer (BJF800, trade name; manufactured by Canon Inc.) to conduct recording on plain paper by means of the ink-jet printer. As a result, a beautiful black print could be obtained.

EXAMPLE 10

The free carboxylic acid type polymer that is a precursor of the sodium salt type carboxylate polymer compound obtained in EXAMPLE 5 was used to prepare a toner composition in the following manner.

After 100 parts by weight of a polyester resin (synthesized from bisphenol A, terephthalic acid, n-dodecenylsuccinic acid, trimellitic acid and diethylene glycol at a molar ratio of 20:38:10:5:27), 70 parts by weight of magnetite ($Fe_3O_4$), 3 parts by weight of the free carboxylic acid type polymer, 2 parts by weight of triphenylmethane dye and 3 parts by weight of low-molecular weight polypropylene were premixed, the resultant premix was melted and kneaded by means of a kneader. After this kneaded product was cooled, it was roughly ground by a Speed mill, then finely ground by a Jet mill, and further classified by means of a zigzag classifier to obtain a toner having a volume average particle diameter of 11 μm.

To 100 parts by weight of this toner were added 0.4 parts by weight of positively charged hydrophobic dry silica treated with amino-modified silicone oil (viscosity at 25° C.: 100 cP; amine equivalent: 800) and 0.2 parts by weight of spherical PVDF particles having an average particle diameter of 0.2 μm, and the resultant mixture was mixed by a Henschel mixer to obtain a positively charged toner composition. This toner composition was used to conduct copying by means of a copying machine, NP-3525 (trade name, manufactured by Canon Inc.). As a result, copying could be beautifully conducted.

EXAMPLE 11

<Synthesis of Monomer B>

Monomer B represented by a structural formula of $CH_2=CHOCH_2CH_2O(CH_2)_6COOC_2H_5$, isobutyl vinyl ether and 2-ethoxyethyl vinyl ether were used.

<Synthesis of Block Polymer Compound>

(1) Synthesis of AB Block Polymer Composed of Isobutyl Vinyl Ether (IBVE: Block Component A) and Monomer B (Block Component B):

After a glass container equipped with a three-way stopcock was purged with nitrogen, it was heated to 250° C. under a nitrogen gas atmosphere to remove adsorbed water. After the system was returned to room temperature, IBVE (12 mmol), ethyl acetate (16 mmol), 1-isobutoxyethyl acetate (0.05 mmol) and toluene (11 ml) were added, and the reaction system was further cooled. Ethylaluminum sesquichloride (equimolar mixture of diethylaluminum chloride and ethylaluminum dichloride; 0.2 mmol) was added at the time the temperature within the system reached 0° C. to initiate polymerization, thereby synthesizing a block segment A of the AB block polymer compound. The molecular weight was time-divisionally monitored by means of molecular sieve column chromatography (GPC) to confirm completion of the polymerization of the component A (IBVE).

A toluene solution of the block component B (10 mmol) was then added to continue the polymerization. After 20 hours, the polymerization reaction was terminated. The termination of the polymerization reaction was conducted by adding a 0.3% by mass aqueous solution of ammonia/methanol into the system. The reaction mixture was diluted with dichloromethane and washed three times with 0.6 M hydrochloric acid and three times with distilled water. The resultant organic layer was concentrated to solids by an evaporator and dried under reduced pressure. The dried product was dialyzed repeatedly by means of a semipermeable membrane in a methanol solvent to remove monomeric compounds, thereby obtaining the intended diblock polymer compound. The compound was identified by means of NMR and GPC. The number average molecular weight (Mn) thereof was 34,500, and the molecular weight dispersity (Mw/Mn) was 1.40.

The block polymer compound thus obtained was hydrolyzed with a mixed aqueous solution of dimethylformamide and sodium hydroxide to obtain a diblock polymer compound that the block segment B was hydrolyzed into a sodium salt. This polymer compound was further neutralized with 0.1N hydrochloric acid in an aqueous dispersion to obtain a diblock polymer compound that the block segment B was converted into a free carboxylic acid. The compound was identified by means of NMR and GPC. The number average molecular weight (Mn) thereof was 32,000, and the molecular weight dispersity (Mw/Mn) was 1.43.

EXAMPLE 12

A block polymer compound was synthesized in the same manner as in EXAMPLE 11 except that 2-ethoxyethyl vinyl ether was used in place of IBVE of the component A in the block polymer compound obtained in EXAMPLE 11. The number average molecular weight (Mn) thereof was 29,500, and the molecular weight dispersity (Mw/Mn) was 1.42.

EXAMPLE 13

Synthesis of a block polymer compound was carried out in the same manner as in EXAMPLE 11 except that $CH_2=CHOCH_2CH_2O(CH_2)_5COOC_2H_5$ having a purity of 99.96% was used in place of the monomer B used in EXAMPLE 11, and a 1:1 (molar ratio) monomer mixture (the number of total moles: 6 mmol) of isobutyl vinyl ether and 2-biphenyloxyethyl vinyl ether was used in place of isobutyl vinyl ether. As a result, a block polymer compound having Mn of 16,700 and Mw/Mn of 1.12 was obtained. Even when $CH_2=CHOCH_2CH_2O(CH_2)_5COOC_2H_5$ having a purity of 99.98% was used, a block polymer compound low in molecular weight dispersity (Mw/Mn=1.09) was obtained likewise. These block polymer compounds were hydrolyzed in the same manner as in EXAMPLE 11 to obtain their corresponding carboxylic acid salt type and free carboxylic acid type block polymer compounds.

EXAMPLE 14

Three parts by weight of a pigment (MOGUL-L, trade name; product of Cabot Co.), 4 parts by weight of the sodium salt type block polymer compound obtained in EXAMPLE 11 and 15 parts by weight of diethylene glycol were added to 78 parts by weight of ion-exchanged water and dispersed therein by means of an ultrasonic homogenizer. The resultant dispersion was filtered under pressure through a filter having a pore size of 1 μm to prepare an ink composition. The dispersibility of the pigment was good.

EXAMPLE 15

The ink composition prepared in EXAMPLE 14 was used to conduct ink-jet recording. The ink composition obtained in EXAMPLE 14 was charged into an ink tank of a Bubble Jet (trademark) printer (BJF800, trade name; manufactured by Canon Inc.) to conduct recording on plain paper by means of the ink-jet printer. As a result, a black recorded article was obtained.

EXAMPLE 16

The block polymer compound obtained in EXAMPLE 12 was hydrolyzed in the same manner as in EXAMPLE 11 to obtain a carboxylic acid salt type block polymer compound. In dimethylformamide were dissolved both 26 parts by mass of this block polymer compound and 10 parts by mass of an oil-soluble dye, Oil Blue N (trade name, product of Aldrich Co.). This oil solution was converted into a water phase using 400 parts by mass of distilled water to obtain an ink composition. Poly(2-ethoxyethyl vinyl ether) segment that is a hydrophobic segment in the block polymer compound is known to become hydrophilic at a low temperature. When this ink composition was cooled to 0° C., the oil-soluble dye, Oil Blue N was deposited by phase separation. This fact revealed that Oil Blue N was enclosed with a polymer micelle.

EXAMPLE 17

In dimethylformamide were dissolved both 26 parts by mass of the carboxylic acid salt type block polymer compound obtained in EXAMPLE 13 and 10 parts by mass of an oil-soluble dye, Oil Blue N (trade name, product of Aldrich Co.). This oil solution was converted into a water phase using 400 parts by mass of distilled water to obtain an ink composition. Although the ink composition was left to stand for 30 days, Oil Blue N was neither separated nor precipitated.

EXAMPLE 18

2N Hydrochloric acid was added to the dispersion obtained in EXAMPLE 11 to adjust its pH to 3, and the viscosity of the resultant composition was measured by means of DAR100 (trade name, manufactured by Rheologica Co.). As a result, the viscosity was increased as greatly as 160 cP. The viscosity of the composition before thickened was lower than 10 cP that is detection limit. The printing test performed in EXAMPLE 15 was carried out on plain paper sprayed with hydrochloric acid. As a result, a beautiful print could be obtained. Even when the surface of the print was strongly rubbed with a line marker, no tailing of the blue ink occurred, so that it was understood that the ink composition has good fixing ability and water fastness.

EXAMPLE 19

The free carboxylic acid type polymer obtained in EXAMPLE 11 was used to prepare a toner composition in the following manner.

After 100 parts by weight of a polyester resin (synthesized from bisphenol A, terephthalic acid, n-dodecenylsuccinic acid, trimellitic acid and diethylene glycol at a molar ratio of 20:38:10:5:27), 70 parts by weight of magnetite ($Fe_3O_4$), 3 parts by weight of the free carboxylic acid type polymer obtained in EXAMPLE 11, 2 parts by weight of triphenylmethane dye and 3 parts by weight of low-molecular weight polypropylene were premixed, the resultant premix was melted and kneaded by means of a kneader. After this kneaded product was cooled, it was roughly ground by a Speed mill, then finely ground by a Jet mill, and further classified by means of a zigzag classifier to obtain a toner having a volume average particle diameter of 11 μm.

To 100 parts by weight of this toner were added 0.4 parts by weight of positively charged hydrophobic dry silica treated with amino-modified silicone oil (viscosity at 25° C.: 100 cP; amine equivalent: 800) and 0.2 parts by weight of spherical PVDF particles having an average particle diameter of 0.2 μm, and the resultant mixture was mixed by a Henschel mixer to obtain a positively charged toner composition. This toner composition was used to conduct copying by means of a copying machine, NP-3525 (trade name, manufactured by Canon Inc.). As a result, black copying could be conducted.

This application claims priorities from Japanese Patent Applications No. 2002-061067 filed on March 6, 2002 and No. 2002-283448 filed on Sep. 27, 2002, which is hereby incorporated by reference herein.

What is claimed is:

1. A block polymer compound having a repeating unit structure represented by the general formula

(15)

wherein B is a linear or branched alkylene group which has 1 to 15 carbon atoms and may be substituted, m is an integer of from 1 to 30, q is an integer of from 2 to 30, and M is a monovalent or polyvalent metal cation, with the proviso that when m is a plural number, the B groups may be different from each other.

2. The block polymer compound according to claim 1, which is amphipatic.

3. A composition comprising the block polymer compound according to claim 1.

4. A composition comprising a solvent or dispersion medium, a functional material and the block polymer compound according to claim 1.

5. A toner composition comprising a dispersion medium, a coloring material and the block polymer compound according to claim 1.

6. An ink composition comprising a solvent, a coloring material and the block polymer compound according to claim 1.

* * * * *